United States Patent
Barnum et al.

(10) Patent No.: US 10,830,774 B2
(45) Date of Patent: Nov. 10, 2020

(54) METHODS AND COMPOSITIONS FOR DIAGNOSIS AND TREATMENT OF MENINGITIS

(71) Applicant: UAB Research Foundation, Birmingham, AL (US)

(72) Inventors: Scott R. Barnum, Birmingham, AL (US); Theresa N. Schein, Birmingham, AL (US); James M. Johnston, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 597 days.

(21) Appl. No.: 15/469,986

(22) Filed: Mar. 27, 2017

(65) Prior Publication Data

US 2017/0261516 A1    Sep. 14, 2017

Related U.S. Application Data

(62) Division of application No. 15/308,573, filed as application No. PCT/US2015/028881 on May 1, 2015.

(60) Provisional application No. 62/116,213, filed on Feb. 13, 2015, provisional application No. 61/988,025, filed on May 2, 2014.

(51) Int. Cl.
    *G01N 33/68*      (2006.01)
    *G01N 33/569*     (2006.01)
    *G01N 33/00*      (2006.01)

(52) U.S. Cl.
    CPC ......... *G01N 33/6893* (2013.01); *G01N 33/00* (2013.01); *G01N 33/56911* (2013.01); *G01N 2333/195* (2013.01); *G01N 2333/4716* (2013.01); *G01N 2800/26* (2013.01); *G01N 2800/28* (2013.01); *G01N 2800/50* (2013.01); *G01N 2800/52* (2013.01)

(58) Field of Classification Search
    None
    See application file for complete search history.

(56) References Cited

U.S. PATENT DOCUMENTS

| 5,778,895 A | 7/1998 | Barnum et al. |
| 2012/0141457 A1 | 6/2012 | Olson et al. |
| 2014/0056808 A1 | 2/2014 | Bansal |

FOREIGN PATENT DOCUMENTS

WO    WO 2011/081421    7/2011

OTHER PUBLICATIONS

Bayston R. (2019) Cerebrospinal Fluid Shunt Infection. In: Cinalli G., Özek M., Sainte-Rose C. (eds) Pediatric Hydrocephalus. Springer, Cham.*

Emlen et al. "Therapeutic complement inhibition: new developments" *Semin. Thromb. Hemost.* 36:(6):660-68 (2010) (Abstract Only).

International Preliminary Report on Patentability corresponding to International Application No. PCT/US2015/028881 (19 pages) (dated Nov. 17, 2016).

International Search Report and the Written Opinion of the International Searching Authority corresponding to International Patent Application No. PCT/US2015/028881 (26 pages) (dated Feb. 3, 2016).

Ramos et al. "Soluble membrane attack complex is diagnostic for intraventricular shunt infection in children" *JCI Insight* 1(10):e87919 (2016).

Ricklin et al. "Complement-targeted therapeutics" *Nat. Biotechnol.* 25(11):1265-75 (2007).

Wagner et al. "Therapeutic potential of complement modulation" *Nat. Rev. Drug Discov.* 9(1):43-56 (2010).

Extended European Search Report corresponding to European Patent Application No. 15786663 (17 pages) (dated Feb. 19, 2018).

Halawa et al. "Terminal component of complement C9 in CSF and plasma of patients with MS and aseptic meningitis" *Acta Neurologica Scandinavica* 80:130-135 (1989).

Lundberg et al. "Presence of vitronectin and activated complement factor C9 on ventriculoperitoneal shunts and temporary ventricular drainage catheters" *Journal of Neurosurgery* 90:101-108 (1999).

Mook-Kanamori et al. "Cerebrospinal fluid complement activation in patients with pneumococcal and meningococcal meningitis" *Journal of Infection* 68:542-547 (2014).

(Continued)

*Primary Examiner* — Brian Gangle
(74) *Attorney, Agent, or Firm* — Myers Bigel, P.A.

(57) ABSTRACT

The present invention provides a method of identifying meningitis as either bacterial meningitis or aseptic meningitis in a subject, comprising: a) measuring the amount of complement C3, complement factor B, complement membrane attack complex (MAC) protein, complement C5b, complement C6, complement C7, complement C8, and/or complement C9 in a cerebrospinal fluid (CSF) sample obtained from the subject; and b) comparing the amount of complement C3, complement factor B, complement MAC protein, complement C5b, complement C6, complement C7, complement C8, and/or complement C9 measured in (a) with the amount of complement C3, complement factor B, complement MAC protein, complement C5b, complement C6, complement C7, complement C8, and/or complement C9 measured in a control sample, wherein an amount of complement C3, complement factor B, complement MAC protein, complement C5b, complement C6, complement C7, complement C8, and/or complement C9 measured in (a) that is greater than the amount of complement C3, complement factor B, complement MAC protein, complement C5b, complement C6, complement C7, complement C8, and/or complement C9 measured in the control sample identifies the meningitis in the subject as bacterial meningitis.

33 Claims, 7 Drawing Sheets

Specification includes a Sequence Listing.

(56) References Cited

OTHER PUBLICATIONS

Woehrl et al. "Complete component 5 contributes to poor disease outcome in humans and mice with pneumococcal meningitis" *Journal of Clinical Investigation* 121(10):3943-3953 (2011).

Gonzalez-Rubio et al. "Complement Factor I Deficiency Associated With Recurrent Meningitis Coinciding with Menstruation" *Archives of Neurology* 58:1923-1928 (2001).

Haerynck, F. "Complement factor B deficiency associated with recurrent meningitis" *La revue de médecine interne* 30:15-16 (2009).

Supplementary Partial European Search Report corresponding to European Patent Application No. 15786663 (16 pages) (dated Oct. 16, 2017).

Tebruegge et al. "Epidemiology, Etiology, Pathogenesis, and Diagnosis of Recurrent Bacterial Meningitis" *Clinical Microbiology Reviews* 21(3):519-537 (2008).

\* cited by examiner

METHODS AND COMPOSITIONS FOR DIAGNOSIS AND TREATMENT OF MENINGITIS

STATEMENT OF PRIORITY

This application is a divisional application of, and claims priority to, U.s. application Ser. No. 15/308,573, which is a 35 U.S.C. § 371 national phase application of International Application Serial No. PCT/US2015/028881, filed May 1, 2015, which claims the benefit, under 35 U.S.C. § 119(e), of U.S. Provisional Application Ser. No. 61/988,025, filed May 2, 2014 and U.S. Provisional Application Ser. No. 62/116,213, filed Feb. 13, 2015, the entire contents of each of which are incorporated by reference herein.

STATEMENT OF GOVERNMENT SUPPORT

This invention was made with government support under grant number NS029719 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5656-61DV_ST25.txt, 796 bytes in size, generated on Dec. 31, 2019 and filed via EFS-Web, is provided in lieu of a paper copy.

FIELD OF THE INVENTION

The present invention relates to methods and compositions for differentiating bacterial meningitis from aseptic meningitis in a subject by detecting changes in the levels of specific complement proteins in the cerebrospinal fluid (CSF) of the subject.

BACKGROUND OF THE INVENTION

Bacterial meningitis remains a major cause of morbidity and mortality, with a high incidence of residual neurological impairment. Early diagnosis and immediate onset of adequate antimicrobial treatment are essential for the survival of patients with bacterial meningitis. However, establishing the diagnosis of bacterial meningitis represents a difficult task in most cases, since clinical signs of acute meningitis are non-specific, and laboratory examinations of cerebrospinal fluid (CSF) often do not accurately differentiate between bacterial and aseptic meningitis. Accurate differentiation between bacterial and aseptic (e.g., viral) meningitis is difficult as both are inflammatory diseases that elicit similar host defense responses and clinical symptoms. Differential diagnosis can be made on positive identification of the bacteria from the cerebrospinal fluid of the affected individual. Unfortunately, it may take several days to grow and identify the bacteria and 25% of the time culture results are negative or equivocal even though the patients have bacterial meningitis. Similar or greater error rates affect nearly every laboratory parameter used for diagnostic purposes.

Due to the beneficial effects of early therapy in bacterial meningitis, antibiotics are often started before etiologic diagnosis is established. As a consequence, a high number of patients with aseptic meningitis receive unnecessary antibiotic treatment, leading to unnecessary and/or prolonged hospitalization, an increased financial burden to the health care system, and exposure of the patient to nosocomial infections and disorders, as well as other hazards associated with hospitalization.

Few laboratory parameters in the cerebrospinal fluid determine bacterial meningitis with absolute certainty, such as positive cerebrospinal fluid culture and Gram staining Although highly specific, these parameters show very low sensitivities and are therefore not useful in ruling out bacterial infection. In addition to microbiological analysis, non-specific parameters in the cerebrospinal fluid are commonly used for the differential diagnosis of bacterial versus aseptic meningitis, such as total and differential cerebrospinal fluid leukocyte count, cerebrospinal fluid protein and glucose concentrations, CSF/serum glucose ratio, cerebrospinal fluid lactate and C-reactive protein levels. However, the diagnostic value of these parameters remains controversial, since their range of distribution overlaps widely in aseptic and bacterial cerebrospinal fluid. The current tests for diagnosing bacterial meningitis take hours to days for completion and have significant false-positive rates. Polymerase chain reaction (PCR) can be employed, but only if specialized equipment and trained lab personnel are available, and the causative agent is in significant quantities in the spinal fluid. Hospital admission of aseptic meningitis patients is unnecessary, adds a significant financial burden to the health care system (estimated at $1-2 B/yr.), and increases the risk of dangerous hospital-acquired infections. There is a critical need for an inexpensive rapid assay that can distinguish between bacterial meningitis and aseptic meningitis.

The present invention overcomes previous shortcomings in the art by providing methods and compositions for differentiating bacterial meningitis from aseptic meningitis in a subject by detecting changes in complement protein levels in CSF of the subject.

SUMMARY OF THE INVENTION

In one aspect, the present invention provides a method of identifying meningitis as either bacterial meningitis or aseptic meningitis in a subject in need thereof, comprising: a) measuring the amount of complement C3, complement factor B, complement MAC (comprising, consisting essentially of or consisting of a complex of complement C5b, complement C6, complement C7, complement C8 and complement C9), complement C5b, complement C6, complement C7, complement C8 and/or complement C9 in a cerebrospinal fluid (CSF) sample obtained from the subject; and b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample identifies the meningitis in the subject as bacterial meningitis.

In another aspect, the present invention provides a method of diagnosing bacterial meningitis in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject; and b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample diagnoses bacterial meningitis in the subject.

A further aspect of the present invention is a method of carrying out a treatment regimen for a subject with meningitis or suspected of having meningitis, comprising: a) measuring the amount of complement C3, complement factor B, complement MAC, complement C5b, complement C6, complement C7, complement C8 and/or complement C9 in a cerebrospinal fluid (CSF) sample obtained from the subject; b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample identifies the meningitis as bacterial meningitis, indicating a treatment regimen of hospitalization and antibiotic therapy and wherein an amount of complement C3, complement factor B, complement MAC, complement C5b, complement C6, complement C7, complement C8 and/or complement C9 that is less than or equal to the amount of complement C3, complement factor B, complement MAC, complement C5b, complement C6, complement C7, complement C8 and/or complement C9 in the control sample identifies aseptic meningitis, indicating a treatment regimen of no hospitalization and no antibiotic therapy; and c) carrying out the indicated treatment regimen.

In an additional aspect, the present invention provides a dry-strip capable of wicking a fluid applied thereto by capillarity within the strip, said strip comprising, in an upstream (at a first end) to downstream (at a second end) direction and in the following order: 1) a sample-application zone, 2) a reaction zone, and 3) a detection zone, wherein said reaction zone comprises a non-immobilized labeled first antibody specific against an epitope of a complement MAC protein, which can be complement C5b, complement C6, complement C7, complement C8 and/or complement C9, effective to form therewith, a mobile complement MAC, which can be complement C5b, complement C6, complement C7, complement C8 and/or complement C9 protein/antibody complex, and said detection zone comprises an immobilized second antibody specific against an epitope of a complement MAC protein, which can be complement C5b, complement C6, complement C7, complement C8 and/or complement C9 protein in said complex, wherein said first and second antibodies are specific for different epitopes on the same complement MAC protein, which can be complement C5b, complement C6, complement C7, complement C8 and/or complement C9 protein and wherein, after application of a body-fluid sample to the sample-application zone at the first end, (i) sample migrates in a downstream direction on the strip toward the reaction zone, (ii) complement MAC protein, which can be complement C5b, complement C6, complement C7, complement C8 and/or complement C9 protein in the sample reacts with the first antibody previously present in the reaction zone to form a mobile, labeled complement MAC, which can be complement C5b, complement C6, complement C7, complement C8 and/or complement C9 protein/antibody complex, (iii) the mobile, labeled complement MAC, which can be complement C5b, complement C6, complement C7, complement C8 and/or complement C9 protein/antibody complex migrates toward the detection zone at the second end, (iv) the mobile, labeled complement MAC, which can be complement C5b, complement C6, complement C7, complement C8 and/or complement C9 protein/antibody complex binds the immobilized second antibody previously present in the detection zone, thereby immobilizing said complex in the detection zone.

Also provided herein is a lateral flow immunoassay device for detecting a marker, comprising: a membrane strip; a detecting antibody that binds a first epitope of the marker; a test line comprising a capturing antibody that binds a second epitope of the marker; and a control line comprising an antibody that binds a control analyte, wherein the marker is selected from the group consisting of complement protein C3, complement protein factor B, complement MAC, complement C5b, complement C6, complement C7, complement C8 and complement protein C9, as well as any combinations thereof.

In addition, the present invention provides a lateral flow immunoassay device comprising: a membrane strip; a first detecting antibody that hinds a first epitope of complement MAC protein, which can be complement C5b, complement C6, complement C7, complement C8 and/or complement C9; a first test line comprising a first capturing antibody that binds a second epitope of complement MAC protein, which can be complement C5b, complement C6, complement C7, complement C8 and/or complement C9; a second detecting antibody that binds a first epitope of complement C3; a second test line comprising a second capturing antibody that binds a second epitope of complement C3; and at least one control line comprising an antibody that binds a control analyte.

Further provided herein is a lateral flow immunoassay device comprising: a membrane strip; a first detecting antibody that binds a first epitope of complement MAC protein, which can be complement C5b, complement C6, complement C7, complement C8 and/or complement C9; a first test line comprising a first capturing antibody that binds a second epitope of complement MAC protein, which can be complement C5b, complement C6, complement C7, complement C8 and/or complement C9; a second detecting antibody that binds a first epitope of complement factor B; a second test line comprising a second capturing antibody that binds a second epitope of complement factor B; and at least one control line comprising an antibody that binds a control analyte.

The present invention also provides a lateral flow immunoassay device comprising: a membrane strip; a first detecting antibody that binds a first epitope of complement MAC protein, which can be complement C5b, complement C6, complement C7, complement C8 and/or complement C9; a first test line comprising a first capturing antibody that binds a second epitope of complement MAC protein, which can be complement C5b, complement C6, complement C7, complement C8 and/or complement C9; a second detecting antibody that binds a first epitope of complement C3; a second test line comprising a second capturing antibody that binds a second epitope of complement C3; a third detecting antibody that binds a first epitope of complement factor B, a third test line comprising a third capturing antibody that binds a second epitope of complement factor B; and at least one control line comprising an antibody that binds a control analyte.

Furthermore, the present invention provides a method of monitoring a subject who is receiving treatment for bacterial meningitis, comprising: (a) obtaining serial samples of cerebrospinal fluid (CSF) from the subject; (b) determining a level of complement MAC protein, which can be complement C5b, complement C6, complement C7, complement C8 and/or complement C9; complement C3 and/or complement factor FB in each of said samples; (c) comparing the level of complement MAC protein, which can be complement C5b, complement C6, complement C7, complement C8 and/or complement C9; complement C3 and/or complement factor FB in the serial samples to detect a change in the level of complement MAC, which can be complement C5b, complement C6, complement C7, complement C8 and/or complement C9; complement C3 and/or complement factor FB over time; and (d) modifying treatment of the subject, based on the results of the comparing step (c).

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted.

Figure 1:
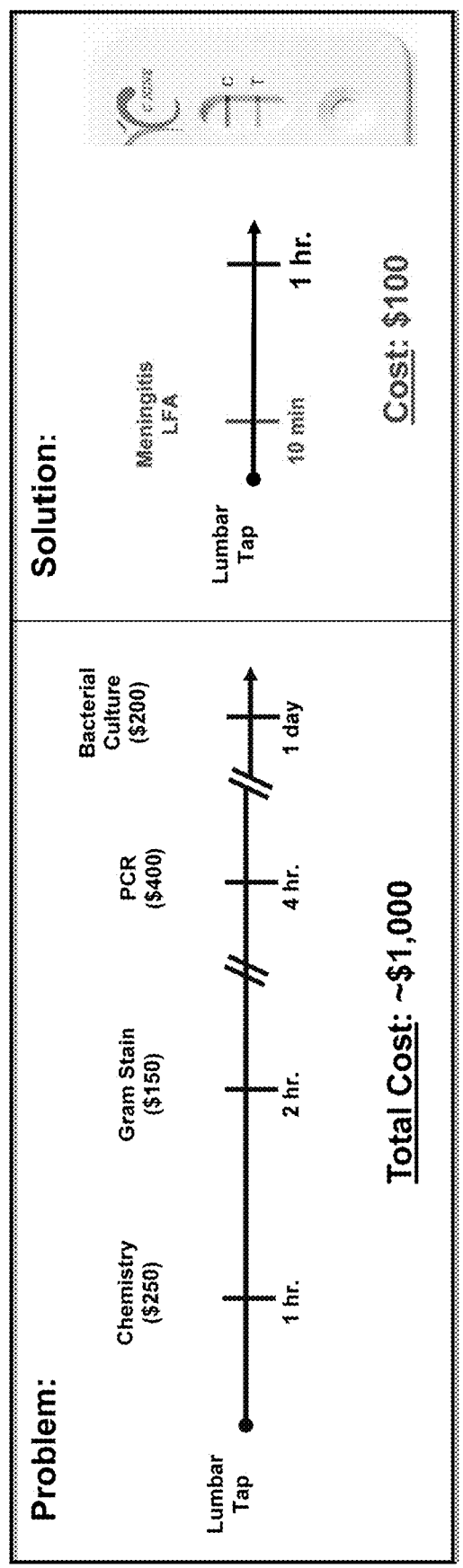
FIG. 1. Comparison of cost and timeframe between a standard diagnostic work up for bacterial meningitis and an exemplary embodiment of the present invention, which is a lateral flow assay, shown in a cassette configuration.

The present invention is based on the unexpected discovery that bacterial meningitis can be differentiated from aseptic meningitis in a subject by detecting changes in the levels of specific complement proteins in the cerebrospinal fluid (CSF) of the subject. In a particular embodiment, the present invention provides a point-of-care, lateral flow assay (LFA) based on bacterial, but not viral, induction of specific complement proteins. The LFA of this invention demonstrates high specificity and sensitivity for diagnosing bacterial meningitis using complement biomarkers. The LFA of this invention offers significant advantages over conventional laboratory methods currently in use, such as 1) ease of use, allowing essentially all medical personnel to perform the assay; 2) rapid, onsite (point-of-care) results available in minutes in the emergency room (ER) or rural/remote clinics or care facilities; 3) substantially reduced clinical laboratory costs; and 4) no specialized equipment, reagents or storage requirements. The diagnostic tests of this invention permit a physician to initiate appropriate treatment regimens, resulting in substantial healthcare cost savings, e.g., by minimizing or preventing unnecessary medical treatment and hospitalization (see, e.g., FIG. 1)

While the complement response is an important defense system against disease, several features make accurate measurement of complement proteins difficult, particularly in a clinically relevant time period. Known technologies require at least about an hour, and often two hours or more to determine complement protein levels. During this time, significant deterioration of a patient's condition may be occurring that does not visibly manifest until significant, or even irreversible, damage has occurred. Additionally, complement proteins are known to be easily activated by handling and other experimental conditions that can significantly affect assay results. Also, the passage of time is a significant factor in spontaneous complement activation, even without handling.

The present invention provides technologies that address these previously unidentified sources of problems. For example, in some embodiments, the present invention provides methods in which relevant steps are all performed within a restricted time period. According to the present invention, such methods provide advantages including minimizing spontaneous complement activation and, alternatively or additionally, providing clinically relevant data within a time period, measured from initiation of sample collection from a subject, that is substantially reduced as compared with standard methodologies. In some embodiments, assays of this invention are completed within a time period, measured from initiation of sample collection from a subject, that is less than about 120 minutes or fewer, 75 minutes or fewer, 60 minutes or fewer, about 50 minutes or fewer, about 40 minutes or fewer, about 30 minutes or fewer, about 20 minutes or fewer, about 10 minutes or fewer, or about 5 minutes or fewer or about 3 minutes or fewer. There is currently no test, assay or protocol available that would allow such a rapid turnaround time, therefore informing physicians in real time regarding diagnosis, treatment and/or further testing. Thus, the present invention provide methods that are substantial improvements over the current protocols for identifying and/or diagnosing subjects of this invention and over the current standard of care and treatment of such subjects.

Complement is notoriously fastidious and can become activated by virtue of standard analysis procedures (handling, storage, and exposure to foreign materials that contact C3 during analysis). Complement is very effective at lysing invading microbes and initiating the wound healing response at sites of injury. This effectiveness is due in part to the ability of C3 to be activated by foreign materials such as bacterial cell wall components. While this property is useful in directing an immune response to new foreign pathogens, this same property presents formidable challenges to experimental and diagnostic study. Materials such as plastics used in sample handling, manipulation of the sample itself, and improper storage conditions can also trigger complement activation. The more processing and handling steps required to perform a given assay, the more false positives can be expected, due to activation of complement by virtue of the assay itself. Such false positives complicate traditional testing and render current testing methods unsuitable for use in directing patient care in near real-time.

The complement system comprises more than 40 serum and cellular proteins and plays important roles in innate and adaptive immunity. There are four major pathways of complement activation. The classical pathway is primarily activated by immune complexes, specifically IgG/IgM antibodies bound to antigen. Other activators include lipopolysaccharide, myelin, polyanionic compounds, C reactive protein (CRP), and microbial DNA and RNA. The lectin pathway is activated by polysaccharides with free-mannose group and other sugars common to fungi and bacteria. The alternative pathway is mediated by direct C3 activation by "foreign" substances that often include microbial cell wall components. All three major pathways of complement activation converge on the central protein complement component 3 (C3). C3 is a central mediator of inflammation and is activated by most factors that cause inflammation. The classical pathway is typically triggered by immune complexes, which are complexes of antigen bound with antibodies, generally belonging to the IgM or IgG isotypes. Immune complexes in turn bind to complement component C1, which is comprised of C1q, C1r, and C1s. The binding of C1q to an antibody-antigen complex triggers activation of C1r and C1s. Activated C1s then cleaves component C4 to produce C4a and C4b. C4b is capable of covalent attachment to cell surfaces, although only about five percent does so. The remaining 95 percent reacts with water to form a soluble, activated C4b. Complement component 2 can then associate with C4b, which after which it is activated by C1s to C2a and C2b. C4b and C2a combine to form C4bC2a, the classical pathway (CP) C3 convertase.

The CP C3 convertase cleaves C3 to form C3a and C3b. Like activated C4b, C3b can covalently bind to cell surfaces or react with $H_2O$ and stay in solution. Activated C3b has multiple roles. By itself, it can serve as an opsonin to make the decorated cell or particle more easily ingested by phagocytes. In addition, C3b can associate with C4bC2a (the CP C3 convertase) to form a C5 convertase. The complex, termed C4bC2aC3b is termed the CP C5 convertase. Alternatively, C3b can form the core of another C3 convertase called the alternative pathway (AP) C3 convertase.

The alternative pathway (AP) is another mechanism by which C3 can become activated. It is typically activated by targets such as microbial surfaces and various complex polysaccharides and other materials. This alternative pathway can also be initiated spontaneously by the cleavage of the thioester bond in C3 by a water molecule to form $C3(H_2O)$. $C3(H_2O)$ binds factor B, which allows factor D to cleave factor B to Ba and Bb. Bb remains associated with $C3(H_2O)$ to form $C3(H_2O)$Bb complex, which acts as a C3 convertase and cleaves C3, resulting in C3a and C3b.

C3b formed either via this process or via the classical or lectin pathways binds to targets (e.g., on cell surfaces) and forms a complex with factor B, which is subsequently cleaved by factor D and form Bb, resulting in C3bBb, which is termed the alternative pathway (AP) C3 convertase. Binding of another molecule of C3b to the AP C3 convertase produces C3bBbC3b, which is the AP C5 convertase.

The lectin complement pathway is initiated by binding of mannose-binding lectin (MBL) and MBL-associated serine protease (MASP) to carbohydrates. The MBL1 gene (known as LMAN1 in humans) encodes a type 1 integral membrane protein localized in the intermediate region between the endoplasmic reticulum and the Golgi complex. The MBL2 gene encodes the soluble mannose-binding protein found in serum. In the human lectin pathway, MASP1 and MASP2 are involved in proteolysis of C4 and C2, leading to C3 convertase, which lead to production of a C5 convertase as described above for the CP.

C5 convertase generated via any of these three pathways cleaves C5 to produce C5a and C5b. C5b then binds to C6, C7, and C8, which catalyses polymerization of C9 to form the C5b-9 membrane attack complex (MAC). The assembling MAC inserts itself into target cell membrane, forming a pore delineated by a ring of C9 molecules. MAC formation causes cell lysis of invading microbes, MAC formation on host cells can also cause lysis, but not necessarily. Sublytic amounts of MAC on the membrane of cells may affect cell function in a variety of ways. The small cleavage products C3a, C4a, and C5a are anaphylatoxins and mediate multiple reactions in the acute inflammatory response. C3a and C5a are also potent chemotactic factors that attract immune system cells such as neutrophils and macrophages into the area of crisis.

The extrinsic protease pathway is a more recently characterized complement activation pathway that directly activates C3 and C5 through the enzymatic action of one or more activated coagulation enzymes including thrombin, plasmin and activated factors IX, X and XII. Activation of C3 and 5 through this pathway generates functionally active C3a, C3b, C5a and C5b in the absence of the canonical C3 and C5 convertases formed through activation of the other three complement pathways.

Complement component C3 is useful as a general alert biomarker that the body is responding to some form of physiological crisis, such as injury, infection, or other disease process. Similarly, complement component C9 is a unique biomarker in the cerebrospinal fluid by virtue of its ability, in association with complement proteins C5b-C9 in the MAC complex, to lyse susceptible bacterial strains that may cause bacterial meningitis. Complement-mediated (C9) lysis results in the release of bacterial cell wall and intracellular components, which directly activate innate immune inflammatory mechanisms that contribute to the severity of meningitis. Complement has been associated with a wide variety of diseases, including lupus, arthritis, intracranial hemorrhage, diabetes, multiple sclerosis, heart disease, and age-related macular degeneration. In many cases, the severity of disease correlates with the level of complement activation. In some cases, complement can play a role in disease pathology. In these cases, the body is not able to successfully control the cause of inflammation, which spreads from local site of injury to systemic inflammation. Complement activation can directly damage tissue or do so indirectly by over-activating cells and recruiting immune cells that in turn cause tissue destruction. Examples of over activation include anaphylactic shock, multiple organ failure (MOF), acute respiratory distress syndrome (ARDS), and systemic inflammatory response syndrome (SIRS).

The assays and methods of the present invention provide several advantages over previous complement assays and methods known in the art. For example, the instant assays and methods are suitable for point-of-care (POC) use, producing results in a matter of minutes, rather than hours. The rapid return of results allows a clinician to act in near real-time to direct patient care. The assays and methods of this invention are easy to use and do not require the availability of a laboratory or a skilled lab technician. Additionally, the assays and methods of this invention require fewer handling steps, and thus minimize complement activation due to handling and processing, which leads to false positive test results.

Thus, in one aspect, the present invention provides a method of identifying meningitis in a subject (e.g., a subject in need thereof) as either bacterial meningitis or aseptic meningitis, comprising: a) measuring the amount of complement C3, complement factor B, complement MAC, complement C5b, complement C6, complement C7, complement C8, and/or complement C9 in a cerebrospinal fluid (CSF) sample obtained from the subject; and b) comparing the amount of complement C3, complement factor B, complement MAC, complement C5b, complement C6, complement C7, complement C8, and/or complement C9 measured in (a) with the amount of complement C3, complement factor B, complement MAC, complement C5b, complement C6, complement C7, complement C8, and/or complement C9 measured in a control sample, wherein an amount of complement C3, complement factor B, complement MAC, complement C5b, complement C6, complement C7, complement C8, and/or complement C9 measured in (a) that is greater than the amount of complement C3, complement factor B, complement MAC, complement C5b, complement C6, complement C7, complement C8, and/or complement C9 measured in the control sample identifies the meningitis in the subject as bacterial meningitis.

In another aspect, the present invention provides a method of diagnosing bacterial meningitis in a subject (e.g., a subject, in need thereof), comprising: a) measuring the amount of complement C3, complement factor B, complement MAC, complement C5b, complement C6, complement C7, complement C8, and/or complement C9 in a cerebrospinal fluid (CSF) sample obtained from the subject; and b) comparing the amount of complement C3, complement factor B, complement MAC, complement C5b, complement C6, complement C7, complement C8, and/or complement C9 measured in (a) with the amount of complement C3, complement factor B, complement MAC, complement C5b, complement C6, complement C7, complement C8, and/or complement C9 measured in a control sample, wherein an amount of complement C3, complement factor B, complement MAC, complement C5b, complement C6, complement C7, complement C8, and/or complement C9 measured in (a) that is greater than the amount of complement C3, complement factor B, complement MAC, complement C5b, complement C6, complement C7, complement C8, and/or complement C9 measured in the control sample diagnoses bacterial meningitis in the subject.

A further aspect of the present invention is a method of carrying out a treatment regimen for a subject with meningitis or suspected of having meningitis (e.g., a subject in need thereof), comprising: a) measuring the amount of complement C3, complement factor B, complement MAC, complement C5b, complement C6, complement C7, complement C8, and/or complement C9 in a cerebrospinal fluid (CSF) sample obtained from the subject; b) comparing the amount of complement C3, complement factor B, complement MAC, complement C5b, complement C6, complement C7, complement C8, and/or complement C9 measured in (a) with the amount of complement C3, complement factor B, complement MAC, complement C5b, complement C6, complement C7, complement C8, and/or complement C9 measured in a control sample, wherein an amount of complement C3, complement factor B, complement MAC, complement C5b, complement C6, complement C7, complement C8, and/or complement C9 measured in (a) that is greater than the amount of complement C3, complement factor B, complement MAC, complement C5b, complement C6, complement C7, complement C8, and/or complement C9 measured in the control sample identifies the meningitis as bacterial meningitis, indicating a treatment regimen of hospitalization and antibiotic therapy and wherein an amount of complement C3, complement factor B, complement MAC, complement C5b, complement C6, complement C7, complement C8, and/or complement C9 that is less than or equal to the amount of complement C3, complement factor B, complement MAC, complement C5b, complement C6, complement C7, complement C8, and/or complement C9 in the control sample identifies aseptic meningitis, indicating a treatment regimen of no hospitalization and no antibiotic therapy; and c) carrying out the indicated treatment regimen.

Nonlimiting examples of other treatment regimens for a subject identified as having bacterial meningitis according to the methods described herein include modifying the duration, type and/or amount of antibiotic therapy; administering ancillary therapies with intravenous fluids, etc.; modifying the duration and/or amount of dexamethasone therapy; administering anti-complement therapy and/or anti-inflammation therapy in combination with or instead of antibiotic therapy; and/or modifying the duration and/or amount of ancillary therapy, anti-complement therapy and/or anti-inflammation therapy. Other treatment regimens that could be modified include the need to perform CT or MRI imaging of the brain (for identification of infarction, abscess, hydrocephalus and other conditions) and repeated CSF analysis in the case of resistant and/or complicated infections.

Many inhibitors of complement are known in the art and suitable for use with the methods of the present invention. In some embodiments, the inhibitor of complement is selected from the group consisting of natural complement inhibitors and derivatives thereof, compstatin and analogs thereof, anti-membrane attack complex (MAC) antibodies, anti-C3 antibodies, anti-C5 antibodies, C3a receptor antagonists, and C5a receptor antagonists. Examples of additional complement inhibitors can be found, for example, in Emlen et al. "Therapeutic complement inhibition: new developments" *Semin. Thromb. Hemost.* 36(6):660-68 (2101); Wagner et al. "Therapeutic potential of complement modulation" *Nat. Rev. Drug Discov.* 9(1):43-56 (2010); and Ricklin et al. "Complement-targeted therapeutics" *Nat. Biotechnol.* 25(11):1265-75 (2007), the contents of each of which are incorporated by reference herein in their entireties.

Nonlimiting examples of other treatment regimens for a subject identified as having aseptic meningitis according to the methods described herein include reducing the duration of hospitalization and/or administration of antibiotics, ancillary therapies, dexamethasone therapy, anti-complement and anti-inflammatory therapies, the need for brain imaging and frequency of contact with a treating physician.

The methods of this invention can also be used to modify standard protocols for diagnosing bacterial meningitis. Currently, the standard diagnostic workup includes a Gram stain, glucose measurement, protein measurement, white blood cell (WBC) count, culture and possibly PCR, all on a CSF sample obtained from a subject. The methods of this invention can be carried out on a CSF sample from a subject as an initial test and if an elevated level of individual components complement C5b, complement C6, complement C7, complement C8, complement C9, the membrane attack complex, (MAC) consisting of C5b-C9, complement C3 and/or complement factor B is detected in the CSF sample, thereby differentiating meningitis in the subject as bacterial meningitis, subsequent tests may include, for example, a Gram stain and/or culture to identify the bacterial pathogen that is causing the bacterial meningitis, e.g., in order to determine the best antibiotic regimen.

In further aspects, the present invention provides a method of identifying meningitis as either bacterial meningitis or aseptic meningitis in a subject in need thereof, comprising: a) measuring the amount of complement C5b, complement C6, complement C7, complement C8, complement C3, complement factor B, complement membrane attack complex (MAC) and/or complement C9 in a cerebrospinal fluid (CSF) sample obtained from the subject; and b) comparing the amount of complement C3, complement factor B, complement MAC, complement C5b, complement C6, complement C7, complement C8, and/or complement C9 measured in (a) with the amount of complement C3, complement factor B, complement MAC, complement C5b, complement C6, complement C7, complement C8, and/or complement C9 measured in a control sample, wherein an amount of complement C3, complement factor B, complement MAC, complement C5b, complement C6, complement C7, complement C8, and/or complement C9 measured in (a) that is greater than an amount of complement C3, complement factor B, complement MAC, complement C5b, complement C6, complement C7, complement C8 and/or complement C9 measured in the control sample identifies the meningitis in the subject as bacterial meningitis.

Also provided herein is a method of identifying meningitis as either bacterial meningitis or aseptic meningitis in a subject in need thereof, comprising measuring the amount of complement C3, complement factor B, complement membrane attack complex (MAC), complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 identifies the meningitis in the subject as bacterial meningitis.

Further provided herein is a method of diagnosing bacterial meningitis in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject; and b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample diagnoses bacterial meningitis in the subject.

The present invention additionally provides a method of diagnosing bacterial meningitis in a subject in need thereof, comprising measuring the amount of complement C3, complement factor B, complement MAC, complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 diagnoses bacterial meningitis in the subject. Additional steps, which can be carried out in some embodiments, include treating the subject with antibiotics and/or other therapeutic agents, hospitalizing the subject, etc.

In further embodiments, the present invention provides a method of diagnosing an infection associated with an indwelling shunt and/or extra-ventricular device in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject; and b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample diagnoses an infection associated with an indwelling shunt and/or extra-ventricular device in the subject. This method allows for the identification of an infection associated with an indwelling shunt and/or extra-ventricular device in a subject that may not be showing symptoms of such an infection and/or for whom a source of infection has not been determined or is difficult to determine. Employing the methods of this invention can inform a physician regarding whether treatment is needed and/or what treatment approach to take. By using the methods described herein, a physician can have information regarding whether the subject has an infection within a much shorter period of time than would occur according to current protocols for diagnosis (e.g., waiting for culture data). Thus, by using the methods of this invention, the subject can receive treatment sooner if an infection is identified or the subject can be spared unnecessary treatment (e.g., with antibiotics), which may be prescribed because an infection is suspected but not yet verified (e.g., by culture results).

A method is also provided herein of diagnosing an infection associated with an indwelling shunt and/or extra-ventricular device in a subject in need thereof, comprising: measuring the amount of complement C3, complement factor B, complement MAC, complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 diagnoses an infection associated with an indwelling shunt and/or extra-ventricular device in the subject.

In further embodiments, the present invention provides a method of diagnosing an autoimmune disorder, traumatic brain injury and/or stroke in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject; and b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample diagnoses an autoimmune disorder, traumatic brain injury and/or stroke in the subject.

A method is also provided herein of diagnosing an autoimmune disorder, traumatic brain injury and/or stroke in a subject in need thereof, comprising: measuring the amount of complement C3, complement factor B, complement MAC, complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 diagnoses an autoimmune disorder, traumatic brain injury and/or stroke in the subject.

Furthermore, the present invention provides a method of identifying a subject as having an increased risk of developing an infection associated with an indwelling shunt and/or extra-ventricular device, comprising: a) measuring the amount of complement C3, complement factor B, complement MAC, complement C5b, complement C6, complement C7, complement C8 and/or complement C9 in a cerebrospinal fluid (CSF) sample obtained from the subject; and b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample identifies the subject as having an increased risk of developing an infection associated with an indwelling shunt and/or extra-ventricular device. By employing the methods of this invention, a subject can be identified who would benefit from medical intervention even if the subject is not manifesting or showing symptoms of a problem or complication or inflammatory condition and/or infection associated with an indwelling shunt and/or extra-ventricular device. Such a subject could be treated prophylactically (e.g., with antibiotics, steroids, anti-inflammatory agents, etc.). A culture of the subject's CSF can be carried out to determine if the subject has an infection and if the culture results identify an infection, the subject can be treated for the infection. A subject identified according to the methods described herein as having an improperly functioning indwelling shunt and/or extra-ventricular device can undergo flushing of the shunt and/or device, removal or replacement of the shunt and/or device, etc. A subject identified according to the methods as described herein can undergo imaging analyses and/or other testing to look for changes in ventrical size, bleeding in the brain, etc. Thus, the benefit of the methods of this invention is that a subject can be identified as a subject in need of such testing and/or medical intervention when there are no other indicators that the subject is in such need. There is currently no test or protocol available to identify such subjects and/or to carry out tests and/or treatments based on information about the levels of complement proteins in the CSF of such subjects.

In addition, the present invention provides a method of identifying a subject as having an increased risk of developing an infection associated with an indwelling shunt and/or extra-ventricular device, comprising measuring the amount of complement C3, complement factor B, complement MAC, complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 measured in the control sample identifies the subject as having an increased risk of developing an infection associated with an indwelling shunt and/or extra-ventricular device.

Also provided herein is a method of guiding a treatment for bacterial meningitis in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject prior to administration of the treatment for bacterial meningitis; b) administering the treatment to the subject; c) measuring the amount of complement C3, complement factor B, complement MAC, complement C5b, complement C6, complement C7, complement C8 and/or complement C9 in a cerebrospinal fluid (CSF) sample obtained from the subject at one or more time points after (b); d) guiding the treatment of the subject for bacterial meningitis using the measurement(s) of (c) such that an increase or no change in the amount(s) measured in (c) relative to the amount(s) measured in (a) leads to a subsequent enhancement of the treatment, and a decrease in the amount(s) measured in (c) relative to the amount(s) measured in (a) leads to no change or a subsequent reduction of the treatment.

Further provided herein is a method of guiding a treatment for an infection associated with an indwelling shunt and/or extra-ventricular device in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject prior to administration of the treatment for the infection associated with an indwelling shunt and/or extra-ventricular device; b) administering the treatment to the subject; c) measuring the amount of complement C3, complement factor B, complement MAC, complement C5b, complement C6, complement C7, complement C8 and/or complement C9 in a cerebrospinal fluid (CSF) sample obtained from the subject at one or more time points after (b); d) guiding the treatment of the subject for the infection associated with an indwelling shunt and/or extra-ventricular device using the measurement(s) of (c) such that an increase or no change in the amount(s) measured in (c) relative to the amount(s) measured in (a) leads to a subsequent enhancement of the treatment, and a decrease in the amount(s) measured in (c) relative to the amount(s) measured in (a) leads to no change or a subsequent reduction of the treatment.

In an additional aspect, the present invention provides a method of guiding a treatment for an autoimmune disorder, traumatic brain injury and/or stroke in a subject in need thereof, comprising: a) measuring the amount of complement C3, complement factor B, complement MAC, complement C5b, complement C6, complement C7, complement C8 and/or complement C9 in a cerebrospinal fluid (CSF) sample obtained from the subject prior to administration of the treatment; b) administering the treatment to the subject; c) measuring the amount of complement C3, complement factor B, complement MAC, complement C5b, complement C6, complement C7, complement C8 and/or complement C9 in a cerebrospinal fluid (CSF) sample obtained from the subject at one or more time points after (b); d) guiding the treatment of the subject for an autoimmune disorder (e.g., multiple sclerosis (MS), systemic lupus erythematosis (SLE) rheumatoid arthritis (RA)), traumatic brain injury and/or stroke (including inflammatory conditions and/or disorders associated with the brain and central nervous system, brain abscess, central nervous system injury) using the measurement(s) of (c) such that an increase or no change in the amount(s) measured in (c) relative to the amount(s) measured in (a) leads to a subsequent enhancement of the treatment, and a decrease in the amount(s) measured in (c) relative to the amount(s) measured in (a) leads to no change or a subsequent reduction of the treatment.

Additionally provided herein is a method of treating a subject with an infection associated with an indwelling shunt and/or extra-ventricular device, comprising: a) measuring the amount of complement C3, complement factor B, complement MAC, complement C5b, complement C6, complement C7, complement C8 and/or complement C9 in a cerebrospinal fluid (CSF) sample obtained from the subject; b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, s complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample identifies an infection in the subject associated with the indwelling shunt and/or extra-ventricular device; and c) treating the subject identified in (b) for the infection associated with the indwelling shunt and/or extra-ventricular device.

Furthermore, the present invention provides a method of treating a subject with an infection associated with an indwelling shunt and/or extra-ventricular device, comprising: a) measuring the amount of complement C3, complement factor B, complement MAC, complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 identifies an infection in the subject associated with the indwelling shunt and/or extra-ventricular device; and b) treating the subject identified in (a) for the infection associated with the indwelling shunt and/or extra-ventricular device.

In an additional embodiment, the present invention provides a method of treating a subject with an improperly functioning indwelling shunt and/or extra-ventricular device, comprising: a) measuring the amount of complement C3, complement factor B, complement MAC, complement C5b, complement C6, complement C7, complement C8 and/or complement C9 in a cerebrospinal fluid (CSF) sample obtained from the subject; b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample identifies an improperly functioning indwelling shunt and/or extra-ventricular device; and c) treating the subject identified in (b) to correct the improperly functioning indwelling shunt and/or extra-ventricular device.

Also provided herein is a method of treating a subject with an improperly functioning indwelling shunt and/or extra-ventricular device, comprising: a) measuring the amount of complement C3, complement factor B, complement MAC, complement C5b, complement C6, complement C7, complement C8 and/or complement C9 in a cerebrospinal fluid (CSF) sample obtained from the subject, wherein an amount of complement C3, complement factor B, complement MAC, complement C5b, complement C6, complement C7, complement C8 and/or complement C9 measured in (a) that is greater than a threshold amount of complement C3, complement factor B, complement MAC, complement C5b, complement C6, complement C7, complement C8 and/or complement C9 identifies an improperly functioning indwelling shunt and/or extra-ventricular device; and b) treating the subject identified in (a) to correct the improperly functioning indwelling shunt and/or extra-ventricular device.

A further embodiment of this invention provides a method of identifying a treatment regimen for a subject with bacterial meningitis, comprising: a) measuring the amount of complement C3, complement factor B, complement MAC, complement C5b, complement C6, complement C7, complement C8 and/or complement C9 in a cerebrospinal fluid (CSF) sample obtained from the subject; b) comparing the amount of complement C3, complement factor B, complement MAC, complement C5b, complement C6, complement C7, complement C8 and/or complement C9 measured in (a) with the amount of complement C3, complement factor B, complement MAC, complement C5b, complement C6, complement C7, complement C8 and/or complement C9 measured in a control sample, wherein an amount of complement C3, complement factor B, complement MAC, complement C5b, complement C6, complement C7, complement C8 and/or complement C9 measured in (a) that is greater than the amount of complement C3, complement factor B, complement MAC, complement C5b, complement C6, complement C7, complement C8 and/or complement C9 measured in the control sample identifies the meningitis as bacterial meningitis, identifying a treatment regimen of hospitalization and antibiotic therapy and wherein an amount of complement C3, complement factor B, complement MAC, complement C5b, complement C6, complement C7, complement C8 and/or complement C9 that is less than or equal to the amount of complement C3, complement factor B, complement MAC, complement C5b, complement C6, complement C7, complement C8 and/or complement C9 in the control sample identifies aseptic meningitis, identifying a treatment regimen of no hospitalization and no antibiotic therapy; and c) carrying out the identified treatment regimen.

The present invention also includes a method of monitoring a subject who is receiving treatment for bacterial meningitis, comprising: a) obtaining serial samples of cerebrospinal fluid (CSF) from the subject prior to initiation of treatment and during treatment; b) measuring a level of complement C5b, complement C6, complement C7, complement C8 complement C9, complement C3, complement MAC and/or complement factor B in each of said samples; c) comparing the level of complement C5b, complement C6, complement C7, complement C8 complement C9, complement C3, complement MAC and/or complement factor B in the serial samples to detect a change in the level of complement C5b, complement C6, complement C7, complement C8 complement C9, complement C3, complement MAC and/or complement factor B over time; and (d) modifying treatment of the subject, based on the results of the comparing.

The present invention further provides a method of monitoring a subject who is receiving treatment for an infection associated with an indwelling shunt and/or extra-ventricular device, comprising: a) obtaining serial samples of cerebrospinal fluid (CSF) from the subject prior to initiation of treatment and during treatment; b) measuring a level of complement C5b, complement C6, complement C7, complement C8 complement C9, complement C3, complement MAC and/or complement factor B in each of said samples; c) comparing the level of complement C5b, complement C6, complement C7, complement C8 complement C9, complement C3, complement MAC and/or complement factor B in the serial samples to detect a change in the level of complement C5b, complement C6, complement C7, complement C8 complement C9, complement C3, complement MAC and/or complement factor B over time; and (d) modifying treatment of the subject, based on the results of the comparing step.

Additionally provided herein is a method of monitoring the status of a subject with an indwelling shunt and/or extra-ventricular device, comprising: a) obtaining serial samples of cerebrospinal fluid (CSF) from the subject; b) measuring a level of complement C5b, complement C6, complement C7, complement C8 complement C9, complement C3, complement MAC and/or complement factor B in each of said samples; c) comparing the level of complement C5b, complement C6, complement C7, complement C8, complement C9, complement C3, complement MAC and/or complement factor B in the serial samples to detect a change in the level of complement C5b, complement C6, complement C7, complement C8 complement C9, complement C3, complement MAC and/or complement factor B over time; and (d) implementing and/or initiating and/or continuing and/or modifying and/or discontinuing treatment of the subject, based on the results of the comparing step.

In some embodiments of the methods of the present invention, only the amount of complement MAC in the CSF sample is measured.

In some embodiments of the methods of the present invention, only the amount of complement C5b in the CSF sample is measured.

In some embodiments of the methods of the present invention, only the amount of complement C6 in the CSF sample is measured.

In some embodiments of the methods of the present invention, only the amount of complement C7 in the CSF sample is measured.

In some embodiments of the methods of the present invention, only the amount of complement C8 in the CSF sample is measured.

In some embodiments of the methods of the present invention, only the amount of complement C9 in the CSF sample is measured.

In some embodiments of the methods of the present invention, only the amount of complement C3 in the CSF sample is measured.

In some embodiments of the methods of the present invention, only the amount of complement factor B in the CSF sample is measured.

In some embodiments of the methods of the present invention, the amount of complement MAC and the amount of complement C9 in the CSF sample are measured.

In some embodiments of the methods of the present invention, the amount of complement MAC and the amount of complement C3 in the CSF sample are measured.

In some embodiments of the methods of the present invention, the amount of complement MAC and the amount of complement factor B in the CSF sample are measured.

In some embodiments of the methods of the present invention, the amount of complement C9 and the amount of complement C3 in the CSF sample are measured.

In some embodiments of the methods of the present invention, the amount of complement C9 and the amount of complement factor B in the CSF sample are measured.

In some embodiments of the methods of the present invention, the amount of complement MAC, the amount of complement factor B and the amount of complement C3 in the CSF sample are measured.

In some embodiments of the methods of the present invention, the amount of complement C9, the amount of complement factor B and the amount of complement C3 in the CSF sample are measured.

In some embodiments of the methods of the present invention, the step of measuring can be carried out with a point of contact (POC) rapid assay system.

In some embodiments of the methods of the present invention, the step of measuring can be carried out with a lateral flow system.

In some embodiments of the methods of the present invention, the step of measuring can be carried out with an immunoassay.

In some embodiments of the methods of the present invention, the step of measuring can be carried out with an enzyme-linked immunosorbent assay (ELISA).

The mean level of complement C3 in a CSF sample of a control (e.g., healthy or non-infected subject) is 2.5 micrograms/ml. In subjects with bacterial meningitis, the mean level of complement C3 in a CSF sample is 48 micrograms/ml. In the methods of the present invention, a reference level of complement C3 in a CSF sample is about 10 micrograms/ml. Therefore, a complement C3 level in a CSF sample of greater than 10 micrograms/ml is increased relative to control and identifies a subject with meningitis as having bacterial meningitis rather than aseptic meningitis. A complement C3 level in a CSF sample of less than 10 micrograms/ml identifies a subject with meningitis as having aseptic meningitis rather than bacterial meningitis.

The mean level of complement factor B (FB) in a CSF sample of a control (e.g., healthy or non-infected subject) is 0.5 micrograms/ml. In subjects with bacterial meningitis, the mean level of complement FB in a CSF sample is 16 micrograms/ml. In the methods of the present invention, a reference level of complement C3 in a CSF sample is about 1.0 microgram/ml. Therefore, a complement FB level in a CSF sample of greater than 1.0 microgram/ml is increased relative to control and identifies a subject with meningitis as having bacterial meningitis rather than aseptic meningitis. A complement FB level in a CSF sample of less than 1.0 microgram/ml identifies a subject with meningitis as having aseptic meningitis rather than bacterial meningitis.

The level of complement C9 in a CSF sample of a control (e.g., healthy or non-infected subject) can be in a range of about 200 ng/ml to about 500 ng/ml. In the methods of the present invention, a reference level of complement C9 in a CSF sample is about 500 ng/ml. Therefore, a complement C9 level in a CSF sample of greater than 500 ng/ml is increased relative to control and identifies a subject with meningitis as having bacterial meningitis rather than aseptic meningitis. A complement C9 level in a CSF sample of less than 500 nanograms/ml identifies a subject with meningitis as having aseptic meningitis rather than bacterial meningitis.

In some embodiments, the level of complement MAC in a CSF sample or a control (e.g., healthy or non-infected subject or subject without an indwelling shunt and/or extra-ventricular device) is less than about 10 ng/ml.

In some embodiments, the level of complement MAC in a CSF sample of a subject with shunt failure and/or a complication associated with an indwelling shunt and/or a subject at increased risk of developing an infection associated with an indwelling shunt and/or extra-ventricular device can be, for example, in the range of about 20 ng/ml to about 100 ng/ml. Thus, in some embodiments, a threshold value for identifying such a subject can be a complement MAC level in CSF of greater than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 75, 100, 125, 150, 200 ng/ml but less than about 240, 245, or 250 ng/ml.

In some embodiments, the level of complement MAC in a CSF sample of a subject with a bacterial infection (e.g., bacterial meningitis, a bacterial infection associated with an indwelling shunt or extra-ventricular device) can be, for example, greater than 250 ng/ml. Thus, in some embodiments, a threshold value for identifying such a subject can be a complement MAC level in CSF of greater than 200, 225, 250, 300, 350, 400, 450, 500, 1000, 2000, 3000, or 4000 ng/ml.

In the methods of this invention, a threshold value can also be determined as a percent increase over a control value, e.g., 5%, 10%, 15%, 20%, 25%, 30%, 35% 40%, 45%, 50%, 60%, 70%, 80%, 90%, 100%, 150%, 200%, 250%, 300%, 400%, 500% or even 1000% greater than or increased over a control value.

Nonlimiting examples of an antibody to complement C3 that can be employed in the methods and assays of this invention include the antibodies listed in Table 1 herein, as well as any other antibody to complement C3 now known or later identified. These antibodies can be used in the methods and assays of this invention in any combination of C3.

Nonlimiting examples of an antibody to complement factor B that can be employed in the methods and assays of this invention include an antibody from Hycult identified as complement factor B/Bb, Human, mAb M13/12, HM2256; an antibody from Comptech identified as Goat Anti-Human Factor B, Catalog No. A235; an antibody from Abcam identified as an Anti-Factor B antibody (ab182924; goat polyclonal to Factor B); an antibody from Abcam identified as an Anti-Factor B antibody (ab72658; rabbit polyclonal to Factor B); and an antibody from Abcam identified as Anti-Factor B antibody (ab190494; goat polyclonal to Factor B), as well as any other antibody to complement factor B now known or later identified. These antibodies can be used in the methods and assays of this invention in any combination of FB antibodies. In some embodiments, the antibody can bind Bb.

Nonlimiting examples of an antibody to complement C9 that can be employed in the methods and assays of this invention include a polyclonal rabbit anti-C9 produced in mouse against the peptide sequence CMPIPVSREEQEQ-HYPIPID (SEQ ID NO:1), This C9 antibody cross reacts with human complement C9, Other examples of an antibody to complement C9 that can be employed in the methods and assays of this invention include an antibody from Hycult identified as C9, Human, mAb X197, HM2111; an antibody from Hycult identified as C9 neoantigen, Human, mAb WU 13-15, HM2264; an antibody from Comptech identified as Goat Anti-Human C9, Catalog No. A226; an antibody from Quidel identified as Goat anti-human C9 #A310: an antibody from Quidel identified as Mouse anti-human C9 #A223; an antibody from Abeam identified as Anti-C9 antibody (ab118902; rabbit polyclonal to C9); an antibody from Abeam identified as Anti-C9 antibody (ab92690; rabbit polyclonal to C9); and an antibody from Abeam identified as Anti-C9 antibody (ab53896; sheep polyclonal to C9), as well as any other antibody to complement C9 now known or later identified. These antibodies can be used in the methods and assays of this invention in any combination of C9.

Nonlimiting examples of an antibody to complement MAC that can be employed in the methods and assays and devices of this invention include an antibody to C5, C5b, C6, C7, C8, C9 and any combination thereof. An antibody to complement MAC can be an antibody that binds C5, C5b, C6, C7, C8 and/or C9 when these respective complement proteins are present in the complement MAC. For example, an antibody to complement MAC can be an antibody that binds to a neo-epitope on complement C9 that is present when complement C9 is part of the complement MAC. An antibody to complement MAC can include an antibody that binds to a neo-epitope present on any of the complement proteins C5, C5b, C6, C7, C8 or C9 when these proteins are part of the complement MAC. Assays and devices of this invention can be employed to detect and/or quantitate any of these antibodies in any combination.

The antibodies to C3, antibodies to FB antibodies to complement MAC and antibodies to C9 as described herein can be employed in the methods and assays of this invention in any combination of C3, FB, MAC and C9 antibodies.

Furthermore, in embodiments of this invention employing antibodies, the antibodies that bind complement C9, the antibodies that bind C3, the antibodies that bind MAC and the antibodies that bind FB are not substantially cross-reactive. The antibodies employed in the methods and assays of this invention can be monoclonal antibodies or polyclonal antibodies, in any combination.

In some embodiments of the methods of this invention, only the amount of complement C9 in the CSF sample is measured. In some embodiments, only the amount of complement C3 in the CSF sample is measured. In some embodiments, only the amount of complement factor B in the CSF sample is measured. In some embodiments, the amount of complement C9 and the amount of complement C3 in the CSF sample are measured. In some embodiments, the amount of complement C9 and the amount of complement factor B in the CSF are measured. In some embodiments, the amount of complement C9 and the amount of complement C3 and the amount of complement factor B in the CSF are measured. In some embodiments, additional complement proteins in the CSF sample can be measured according to the methods described herein, in any combination with, or independent of, measurement of complement C9, complement C3 and/or complement factor B. Thus, nonlimiting examples of complement proteins that can be detected and/or measured singly or in any combination according to the methods of this invention include C3, C9, factor B (FB), C5a, C5b, C3a, C8-alpha, C8-beta, C8-gamma, C7, C4, C6, membrane attack complex (MAC), mannose binding protein (MBP) and MBP-associated serine protease 1 (MASP-1). These complement proteins can be detected and/or measured singly or in any combination.

In some embodiments of this invention, the methods described herein are carried out using an immunoassay system. In some embodiments, the methods described herein are carried out using a point-of-contact (POC) rapid assay system. In some embodiments, the methods of this invention are carried out using an enzyme-linked immunosorbent assay (ELISA). In some embodiments, the methods of this invention are carried out using a lateral flow system.

In one embodiment, the present invention provides a dry-strip capable of wicking a fluid applied thereto by capillarity within the strip, said strip comprising, in an upstream (at a first end) to downstream (at a second end) direction and in the following order: 1) a sample-application zone, 2) a reaction zone, and 3) a detection zone, wherein said reaction zone comprises a non-immobilized labeled first antibody specific against an epitope of a complement C9 protein, effective to form therewith, a mobile complement C9 protein/antibody complex, and said detection zone comprises an immobilized second antibody specific against an epitope of a complement C9 protein in said complex, wherein said first and second antibodies are specific for different epitopes on the same complement C9 protein and wherein, after application of a body fluid sample to the sample-application zone at the first end, (i) sample migrates in a downstream direction on the strip toward the reaction zone, (ii) complement C9 protein in the sample reacts with the first antibody previously present in the reaction zone to form a mobile, labeled complement C9 protein/antibody complex, (iii) the mobile, labeled complement C9 protein/antibody complex migrates toward the detection zone at the second end, (iv) the mobile, labeled complement C9 protein/antibody complex binds the immobilized second antibody previously present in the detection zone, thereby immobilizing said complex in the detection zone. In some embodiments of the dry-strip of this invention, the first antibody and second antibody are present on the dry-strip prior to application of the body fluid sample to the dry-strip. In some embodiments the first antibody is a monoclonal antibody and in some embodiments the second antibody is a monoclonal antibody. In some aspects, both the first antibody and the second antibody are monoclonal antibodies.

In one embodiment, the present invention provides a dry-strip capable of wicking a fluid applied thereto by capillarity within the strip, said strip comprising, in an upstream (at a first end) to downstream (at a second end) direction and in the following order: 1) a sample-application zone, 2) a reaction zone, and 3) a detection zone, wherein said reaction zone comprises a non-immobilized labeled first antibody specific against an epitope of a complement C3 protein, effective to form therewith, a mobile complement C3 protein/antibody complex, and said detection zone comprises an immobilized second antibody specific against an epitope of a complement C3 protein in said complex, wherein said first and second antibodies are specific for different epitopes on the same complement C3 protein and wherein, after application of a body fluid sample to the sample-application zone at the first end, (i) sample migrates in a downstream direction on the strip toward the reaction zone, (ii) complement C3 protein in the sample reacts with the first antibody previously present in the reaction zone to form a mobile, labeled complement C3 protein/antibody complex, (iii) the mobile, labeled complement C3 protein/antibody complex migrates toward the detection zone at the second end, (iv) the mobile, labeled complement C3 protein/antibody complex binds the immobilized second antibody previously present in the detection zone, thereby immobilizing said complex in the detection zone. In some embodiments of the dry-strip of this invention, the first antibody and second antibody are present on the dry-strip prior to application of the body fluid sample to the dry-strip. In some embodiments the first antibody is a monoclonal antibody and in some embodiments the second antibody is a monoclonal antibody. In some aspects, both the first antibody and the second antibody are monoclonal antibodies.

In one embodiment, the present invention provides a dry-strip capable of wicking a fluid applied thereto by capillarity within the strip, said strip comprising, in an upstream (at a first end) to downstream (at a second end) direction and in the following order: 1) a sample-application zone, 2) a reaction zone, and 3) a detection zone, wherein said reaction zone comprises a non-immobilized labeled first antibody specific against an epitope of a complement factor B (FB) protein, effective to form therewith, a mobile complement FB protein/antibody complex, and said detection zone comprises an immobilized second antibody specific against an epitope of a complement FB protein in said complex, wherein said first and second antibodies are specific for different epitopes on the same complement FB protein and wherein, after application of a body fluid sample to the sample-application zone at the first end, (i) sample migrates in a downstream direction on the strip toward the reaction zone, (ii) complement FB protein in the sample reacts with the first antibody previously present in the reaction zone to form a mobile, labeled complement FB protein/antibody complex, (iii) the mobile, labeled complement FB protein/antibody complex migrates toward the detection zone at the second end, (iv) the mobile, labeled complement FB protein/antibody complex binds the immobilized second antibody previously present in the detection zone, thereby immobilizing said complex in the detection zone. In some embodiments of the dry-strip of this invention, the first antibody and second antibody are present on the dry-strip prior to application of the body fluid sample to the dry-strip. In some embodiments the first antibody is a monoclonal antibody and in some embodiments the second antibody is a monoclonal antibody. In some aspects, both the first antibody and the second antibody are monoclonal antibodies.

In one embodiment, the present invention provides a dry-strip capable of wicking a fluid applied thereto by capillarity within the strip, said strip comprising, in an upstream (at a first end) to downstream (at a second end) direction and in the following order: 1) a sample-application zone, 2) a reaction zone, and 3) a detection zone, wherein said reaction zone comprises a non-immobilized labeled first antibody specific against an epitope of a complement MAC protein, which can be complement C5b, complement C6, complement C7, complement C8 and/or complement C9, effective to form therewith, a mobile complement protein/antibody complex, and said detection zone comprises an immobilized second antibody specific against an epitope of a complement MAC protein, which can be complement C5b, complement C6, complement C7, complement C8 and/or complement C9, in said complex, wherein said first and second antibodies are specific for different epitopes on the same complement protein and wherein, after application of a body fluid sample to the sample-application zone at the first end, (i) sample migrates in a downstream direction on the strip toward the reaction zone, (ii) complement protein in the sample reacts with the first antibody previously present in the reaction zone to form a mobile, labeled complement protein/antibody complex, (iii) the mobile, labeled complement protein/antibody complex migrates toward the detection zone at the second end, (iv) the mobile, labeled complement protein/antibody complex binds the immobilized second antibody previously present in the detection zone, thereby immobilizing said complex in the detection zone. In some embodiments of the dry-strip of this invention, the first antibody and second antibody are present on the dry-strip prior to application of the body fluid sample to the dry-strip. In some embodiments the first antibody is a monoclonal antibody and in some embodiments the second antibody is a monoclonal antibody. In some aspects, both the first antibody and the second antibody are monoclonal antibodies.

In the embodiments of the dry-strip described herein, the dry-strip can be configured to detect or measure a single complement protein in the sample (e.g., only C3, C5b, C6, C7, C8, C9, MAC or FB) or configured to detect or measure two or more (e.g., 2, 3, 4, 5, 6, 7, 8, 9, 10, etc.) complement proteins (e.g., C3 and C9, C3 and FB, C9 and FB, C3 and C9 and FB, C3 and one or more MAC proteins, FB and one or more MAC proteins, two or more of any of the MAC proteins C5b, C6, C7, C8 and C9) in any combination. The two or more complement proteins can be detected on the dry-strip in series or in parallel. For example, multiple dry-strips can be arranged in parallel and/or multiple test lines can be arranged in series on a single dry-strip.

In further embodiments, the present invention provides a lateral flow immunoassay device for detecting a marker, comprising: a membrane strip; a detecting antibody that binds a first epitope of the marker; a test line comprising a capturing antibody that binds a second epitope of the marker; and a control line comprising an antibody that binds a control analyte, wherein the marker is selected from the group consisting of complement protein C3, complement protein factor B, complement MAC, complement C5b, complement C6, complement C7, complement C8 and/or complement protein C9, singly or in any combination.

In addition, the present invention provides a lateral flow immunoassay device comprising: a membrane strip; a first detecting antibody that binds a first epitope of complement C9; a first test line comprising a first capturing antibody that binds a second epitope of complement C9; a second detecting antibody that binds a first epitope of complement C3; a second test line comprising a second capturing antibody that binds a second epitope of complement C3; and at least one control line comprising an antibody that binds a control analyte.

Further provided herein is a lateral flow immunoassay device comprising: a membrane strip; a first detecting antibody that binds a first epitope of complement C9; a first test line comprising a first capturing antibody that binds a second epitope of complement C9; a second detecting antibody that binds a first epitope of complement factor B; a second test line comprising a second capturing antibody that binds a second epitope of complement factor B; and at least one control line comprising an antibody that binds a control analyte.

The present invention also provides a lateral flow immunoassay device comprising: a membrane strip; a first detecting antibody that binds a first epitope of complement C9; a first test line comprising a first capturing antibody that binds a second epitope of complement C9; a second detecting antibody that binds a first epitope of complement C3; a second test line comprising a second capturing antibody that binds a second epitope of complement C3; a third detecting antibody that binds a first epitope of complement factor B, a third test line comprising a third capturing antibody that binds a second epitope of complement factor B; and at least one control line comprising an antibody that binds a control analyte.

In additional embodiments, the present invention provides a dry-strip capable of wicking a fluid applied thereto by capillarity within the strip, said strip comprising, in an upstream (at a first end) to downstream (at a second end) direction and in the following order: 1) a sample-application zone, 2) a reaction zone, and 3) a detection zone, wherein said reaction zone comprises a non-immobilized labeled first antibody specific against an epitope of a complement MAC protein (e.g., C5b, C6, C7, C8 and/or C9, effective to form therewith, a mobile complement MAC/antibody complex, and said detection zone comprises an immobilized second antibody specific against an epitope of a complement MAC in said complex, wherein said first and second antibodies are specific for different epitopes on the same complement MAC and wherein, after application of a body-fluid sample to the sample-application zone at the first end, (i) sample migrates in a downstream direction on the strip toward the reaction zone, (ii) complement MAC in the sample reacts with the first antibody previously present in the reaction zone to form a mobile, labeled complement MAC/antibody complex, (iii) the mobile, labeled complement MAC/antibody complex migrates toward the detection zone at the second end, (iv) the mobile, labeled complement MAC/antibody complex binds the immobilized second antibody previously present in the detection zone, thereby immobilizing said complex in the detection zone.

Also provided herein is a lateral flow immunoassay device for detecting a marker, comprising: a membrane strip; a detecting antibody that binds a first epitope of the marker; a test line comprising a capturing antibody that binds a second epitope of the marker; and a control line comprising an antibody that binds a control analyte, wherein the marker is selected from the group consisting of complement protein C3, complement protein factor B, complement MAC, complement protein C9 and any combination thereof. Such a lateral flow immunoassay device can comprise a detecting antibody that comprises a label that provides a signal, e.g., for detection and/or quantitation, as is well known in the art.

In further embodiments, the present invention provides a lateral flow immunoassay device comprising: a membrane strip; a first detecting antibody that binds a first epitope of a first protein selected from the group consisting of complement C9, complement C3, complement protein factor B and complement MAC; a first test line comprising a first capturing antibody that binds a second epitope of the first protein; a second detecting antibody that binds a first epitope of a second protein selected from the group consisting of complement C9, complement C3, complement protein factor B and complement MAC, wherein said second protein is different from said first protein; a second test line comprising a second capturing antibody that binds a second epitope of the second protein; and at least one control line comprising an antibody that binds a control analyte.

In some embodiments, the lateral flow immunoassay device described herein can further comprise a third detecting antibody that binds a first epitope of a third protein selected from the group consisting of complement C9, complement C3, complement protein factor B and complement MAC, wherein said third protein is different from said first protein and said second protein, and a third test line comprising a third capturing antibody that binds a second epitope of the third protein.

In yet further embodiments, the lateral flow immunoassay device described herein can comprise a fourth detecting antibody that binds a first epitope of a fourth protein selected from the group consisting of complement C9, complement C3, complement protein factor B and complement MAC (e.g., C5b, C6, C7, C8 and/or C9), wherein said fourth protein is different from said first protein and said second protein and said third protein, and a fourth test line comprising a fourth capturing antibody that binds a second epitope of the forth protein.

The lateral flow immunoassay device described herein can comprise detecting antibodies wherein each respective detecting antibody comprise a label that provides a different signal that distinguishes each of said detecting antibodies from one another.

Furthermore, the present invention provides a method of monitoring a subject who is receiving treatment for bacterial meningitis, comprising: (a) obtaining serial samples of cerebrospinal fluid (CSF) from the subject; (b) determining a level of complement C9, complement C3, complement MAC, which can be C5b, C6, C6, C8 and/or C9; and/or complement factor B in each of said samples; (c) comparing the level of complement C9, complement C3, complement MAC, which can be C5b, C6, C6, C8 and/or C9; and/or complement factor B in the serial samples to detect a change in the level of complement C9, complement C3, complement MAC, which can be C5b, C6, C6, C8 and/or C9; and/or complement factor B over time; and (d) modifying treatment of the subject, based on the results of the comparing step (c). Such modifying can include, for example, initiating treatment, enhancing treatment, resuming treatment, maintaining treatment, reducing treatment, halting treatment, etc., pursuant to the results of the comparison. For example, in some embodiments, an increase over time would lead to initiating treatment, enhancing treatment, resuming treatment, or maintaining treatment. In some embodiments, a decrease over time would lead to reducing treatment or halting treatment.

For example, the clinician may detect a decrease in one or more complement proteins of this invention in a sample from the subject during treatment of the subject. Accordingly, the clinician may then modify the subject's treatment by adjusting the dosing of medications administered, such as antibiotics, anti-inflammatory agents and/or complement inhibitors, or by discontinuing treatment once complement levels have returned to normal.

In other embodiments, the clinician may detect an increase in one or more (e.g., 2, 3, 4, 5, 6, 7, 8, 9, 10, etc.) complement proteins of this invention in a sample from a subject during treatment of the subject. Accordingly, the clinician may then modify the subject's treatment regimen, e.g., by increasing the dosage of medications, such as antibiotics, anti-inflammatory agents and/or complement inhibitors, until a desired stabilization or decrease in complement protein level(s) is achieved. If no change in complement protein level is detected in a sample from the subject during treatment, the clinician may modify the subject's treatment regimen or may maintain the subject's treatment regimen until a change in complement protein levels is observed.

A lateral flow immunoassay device embodiment of the present invention is described herein and is comprised of a cellulose membrane strip, upon which is disposed a sample pad to absorb the sample fluid and allow gradual migration of the sample-and-particle-conjugate immune complexes, a wick at the distal end of the strip that absorbs the liquid sample and conjugate material to facilitate capillary migration through the cellulose membrane strip, and a particle conjugate pad comprising a detecting antibody bound to a label, or detection conjugate. The cellulose membrane strip is the test zone region, upon which is disposed a test line, comprising monoclonal or polyclonal antibodies striped for capturing the detection conjugate and a control line, comprising an antibody that binds a control analyte, such as IgG, and indicates to the user that the test was successfully run. The lateral flow immunoassay further comprises a polyester film backing attached to the cellulose membrane strip, and a pressure-sensitive laminate film backing. Each lateral flow immunoassay may be packaged in a MYLAR zero-vapor barrier pouch, for example.

When a test sample is applied to the sample pad, the sample migrates from the sample pad through the particle conjugate pad, where any target analyte present will bind to the detecting antibody conjugate. The sample then continues to migrate across the membrane until it reaches the test line where the target/conjugate complex will bind to the immobilized antibodies producing a visible line on the membrane. The sample then migrates further along the membrane strip until it reaches the control line, where excess antibody conjugate that did not bind the test line will bind the control line and produce a second visible line on the membrane. The control line ligand is often an antibody against the Fc region of the conjugated antibody. This control line indicates that the sample has migrated across the membrane as intended.

In certain embodiments, a lateral flow immunoassay device in accordance with the present invention comprises a single membrane strip for the detection of a single analyte. In other embodiments, the lateral flow immunoassay detects two or more (e.g., 2, 3, 4, 5, 6, 7, 8, 9, 10, etc.) analytes. When the lateral flow immunoassay detects two or more analytes, the test can be configured with multiple membrane strips arranged in parallel or with multiple test lines arranged in series on a single membrane strip.

In some embodiments, the lateral flow immunoassay is configured to test for two analytes in a single test cassette in parallel. In some embodiments, the lateral flow immunoassay comprises two ports for instilling the test samples and a separate membrane strip for each analyte. In other embodiments, the lateral flow immunoassay comprises one port for instilling the sample and a separate membrane strip for each analyte.

In some embodiments, the lateral flow immunoassay device may be configured to test for three analytes in a single test cassette in parallel. In some embodiments, the lateral flow immunoassay may comprise three ports for instilling the test sample and a separate membrane strip for each analyte. In other embodiments, the lateral flow immunoassay may comprise one port for instilling the test sample and a separate membrane strip for each analyte.

In certain embodiments, the lateral flow immunoassay device may be configured to test for multiple analytes in a single test cassette in series, e.g. a test cassette comprising a membrane strip with two test lines and one control line arranged in series or a test cassette comprising a membrane strip with three test lines and one control line arranged in series.

The lateral flow immunoassay device presently disclosed may provide qualitative and/or quantitative detection of the target markers. Qualitatively, two clear lines on the membrane may represent a positive result, whereas a single line in the control zone may represent a negative result. Quantitatively, the level or amount of the target markers can be determined in samples based on comparison with standard curves developed individually for each target and run prior to test sample assaying.

In some embodiments, the detecting antibody comprises a label that provides a signal that can be read visually by a clinician or electronically via a commercial reader or electronically via an internal reader array on a printed circuit board installed within a lateral flow assay cassette. Various labels are suitable for use in the instantly disclosed assays. In a specific embodiment, the label may be colloidal gold.

One skilled in the art will appreciate that various control analytes are suitable for use in the methods of the instant invention to provide verification that the assay was successfully completed. In one embodiment, the control analyte is IgG.

In some embodiments of the present methods, it is desirable to have a lateral flow immunoassay that can detect more than complement protein in a single assay. For example, a dual lateral flow immunoassay that can qualitatively and quantitatively detect C9 in addition to C3, MAC or FB in the same aliquot of a body fluid may be highly desirable. Hence, in another embodiment, a lateral flow immunoassay for the point-of-care detection of complement proteins in a body fluid sample comprising complement proteins is provided, the lateral flow immunoassay device comprising: a membrane strip; a first detecting antibody that binds a first epitope of complement C9; a first test line comprising a first capturing antibody that binds a second epitope of complement C9; a second detecting antibody that binds a first epitope of C3, MAC or FB; a second test line comprising a second capturing antibody that binds a second epitope of C3 or FB; and at least one control line comprising an antibody that binds a control analyte.

In some embodiments a lateral flow immunoassay that can qualitatively and quantitatively detect C9 in addition to C3, MAC and FB in the same aliquot of a body fluid may be highly desirable. Hence, in another embodiment, a lateral flow immunoassay device for the point-of-care detection of complement proteins in a body fluid sample comprising complement proteins is provided, the lateral flow immunoassay device comprising: a membrane strip; a first detecting antibody that binds a first epitope of complement C9; a first test line comprising a first capturing antibody that binds a second epitope of complement C9; a second detecting antibody that binds a first epitope of C3; a second test line comprising a second capturing antibody that binds a second epitope of C3; a third detecting antibody that binds a first epitope of complement FB, a third test line comprising a third capturing antibody that binds a second epitope of complement FB; and at least one control line comprising an antibody that binds a control analyte. Additional test lines can be included comprising antibodies that bind complement MAC proteins, which can be complement C5b, complement C6, complement C7, complement C8 and/or complement C9. Such a lateral flow assay of this invention can comprise antibodies to complement C3, complement C5b, complement C6, complement C7, complement C8, complement C9 and/or complement FB in any combination and in any order of first antibodies, second antibodies, third antibodies, etc. in the appropriate configuration as would be known to one of ordinary skill in the art.

There is a wide variety of labels that may be used with a binding moiety (antibody or antigen) to form a labeled reagent. The choice of the label depends on the sensitivity required, ease of conjugation with the binding moiety, stability requirements, available instrumentation, and disposal provisions. Labels of the present invention may be soluble or particulate, metallic, organic, or inorganic, and may include spectral labels such as green fluorescent protein, fluorescent dyes (e.g., fluorescein and its derivatives, rhodamine and its derivatives, biotin, avidin, and streptavidin), chemiluminescent compounds (e.g., luciferin and luminol); and enzymes (e.g., horseradish peroxidase, alkaline phosphatase, etc.), spectral colorimetric labels such as colloidal gold, or carbon particles, or colored glass or plastic (e.g., polystyrene, polypropylene, latex, etc.) beads.

The label can be coupled directly or indirectly to a component of the binding moiety according to methods well known in the art, such as those described in U.S. Pat. Nos. 4,863,875 and 4,373,932, each of which is incorporated herein by reference. Non-radioactive labels are often attached by indirect means. Generally, a ligand molecule (e.g., biotin) is covalently bound to the binding moiety. The ligand then binds to an anti-ligand (e.g., streptavidin) molecule which is either inherently detectable or is covalently bound to a signal system such as a detectable enzyme, a fluorescent compound, or a chemiluminescent compound. The label may be attached to the binding moiety by a chemical linker. Linker domains are typically polypeptide sequences, such as poly-gly sequences of between about 5 and 200 amino acids. Preferred linkers are often flexible amino acid sub-sequences. Such flexible linkers are known to persons skilled in the art. For example, poly(ethylene glycol) is available commercially (Shearwater Polymers, Inc. Huntsville, Ala.). The detection moiety can also be conjugated directly to the signal-generating compound, e.g., by conjunction with an enzyme or fluorophore.

The presence of a label can be detected by inspection, or a detector that monitors a particular probe or probe combination. Typical detectors include spectrophotometers, phototubes and photodiodes, microscopes, scintillation counters, cameras, film and the like, as well as combinations thereof. Examples of suitable detectors are widely available from a variety of commercial sources known to persons skilled in the art.

For purposes of the present invention, preferred labels are non-radioactive and are readily detected without the use of sophisticated instrumentation. Preferably, the labels will yield a visible signal that is immediately discernable upon visual inspection, or by fluorescence detection. Preferred labels include those that may be observed as: 1) chemiluminescence (using horseradish peroxidase and/or alkaline phosphatase with substrates that produce photons as breakdown products); 2) color change (colloidal gold, which produces a colored precipitate with the immuno-reactive event), and 3) fluorescence (using, e.g., fluorescein, and other fluorescent tags). In one preferred embodiment of the invention, colloidal gold is used as the label and the label is directly conjugated to the binding moiety (the antibody or antigen). When gold is used as the label, the reaction of labeled reagent-analyte complex with the capture reagent results in the appearance of a red colored deposit. As will be appreciated by one of skill in the art, the color that appears upon the reaction of the complex with the capture reagent immobilized at the capturing zone will depend on the label used.

In one embodiment of an assay format of the invention, the capture and control capture reagents are immobilized on a solid substrate. There are a variety of solid supports known to the art, which are suitable for use with the present invention. For instance, the solid support may be beads, membranes (e.g., nitrocellulose), microtiter wells (e.g., PVC or polystyrene), strings, plastic, strips, or any surface onto which antibodies may be deposited or immobilized. In addition, a wide variety of organic and inorganic polymers, both natural and synthetic, may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers, which form several aqueous phases, such as dextrans and polyalkylene glycols or surfactants, such as phospholipids or long chain (12-24 carbon atoms) alkyl ammonium salts and the like are also suitable.

The manner of linking a wide variety of compounds to various surfaces is well known and is amply illustrated in the literature. See, for example, IMMOBILIZED ENZYMES, Ichiro Chibata, Halsted Press, New York, 1978, and Cuatrecasas, 1970, the disclosures of which are incorporated herein by reference. The capturing and control reagents may be covalently bound or non-covalently attached through nonspecific bonding. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components.

In one embodiment of the invention, the capture and control reagents are nonspecifically absorbed on a nitrocellulose membrane and blocked by a blocking buffer (e.g., 0.5% BSA; 4% sucrose in PBS).

The present invention also provides a kit comprising a dry-strip or lateral flow assay cassette or composition of this invention, in combination with reagents and instructions for use.

Definitions

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

A "subject" of this invention includes, but is not limited to, any animal that is susceptible to meningitis, including for example, humans, non-human primates, horses, cows, cats, dogs, pigs, rats, and mice. Administration of the various compositions of this invention can be accomplished by any of several different routes. In specific embodiments, the compositions can be administered intramuscularly, subcutaneously, intraperitoneally, intradermally, intranasally, intracranially, sublingually, intravaginally, intrarectally, orally, or topically. The compositions herein may be administered via a skin scarification method, or transdermally via a patch or liquid. The compositions can be delivered subdermally in the form of a biodegradable material that releases the compositions over a period of time.

"Bacterial meningitis" means meningitis (i.e., inflammation of the meninges) caused by any bacterial species including but not limited to *Streptococcus* sp., *Escherichia* sp., *Staphylococcus* sp., *Listeria* sp., *Neisseria* sp., *Salmonella* sp. *Haemophilus* sp., and other Gram-negative and Gram-positive bacteria.

When bacteria are not causing the inflammation or if the bacterial organism cannot be grown and identified in the laboratory, it is called "aseptic meningitis." Thus, aseptic meningitis is typically due to infection by agents other than bacteria, which can be, for example, Coxsackie viruses, echoviruses, adenovirus, enteroviruses, herpesviruses, mumps virus, rabies virus other unspecified viruses, cryptococcal infection or infection due to other fungal organisms and infection due to parasites. Aseptic meningitis, also known as sterile meningitis, has also been associated, in some cases, with autoimmune disease, cancer, Lyme disease, or an adverse reaction to medication. Meningitis can also be caused by mycobacterial species and is considered to be aseptic meningitis.

Symptoms of bacterial meningitis and aseptic meningitis in adults are similar and can include, but are not limited to fever, headache, stiff neck, decreased consciousness, seizures, eye sensitivity and/or pain, rash, dizzy spells and vomiting. In babies, the signs of meningitis may be a fever, irritability that is difficult to calm, decreased appetite, rash, vomiting, and a shrill cry. Babies also may have a stiff body and bulging soft spots on the head that aren't caused by crying. Babies with meningitis may cry when handled. Young children with meningitis may act like they have the flu (influenza), cough, or have trouble breathing. Older adults and people with other medical conditions may have only a slight headache and fever. They may not feel well and may have little energy.

Thus, a "subject in need thereof" as described herein is a subject that has symptoms of meningitis and/or has been diagnosed with meningitis and/or is suspected of having meningitis and/or has been exposed to or had contact with other subjects with symptoms of meningitis and/or have been diagnosed with and/or are suspected of having meningitis.

The term "analyte" means any entity, particularly a chemical, biochemical or biological entity to be assessed, e.g., whose amount (e.g., concentration or mass), activity, composition, or other property(ies) is/are to be detected, measured, quantified, evaluated, analyzed, etc. An "analyte" can be a single molecular species or can be composed of multiple distinct molecular species.

The term "antibody" encompasses intact and/or full length immunoglobulins of types IgA, IgG (e.g., IgG1, IgG2, IgG3, IgG4), IgE, IgD, IgM, IgY, antigen-binding fragments or single chains of complete immunoglobulins (e.g., single chain antibodies, Fab fragments, F(ab')2 fragments, Fd fragments, scFv (single-chain variable), and dAb fragments), and other proteins that include at least one antigen-binding immunoglobulin variable region, e.g., a protein that comprises an immunoglobulin variable region, e.g., a heavy (H) chain variable region (VH) and a light (L) chain variable region (VL). The light chains of an antibody may be of type kappa or lambda. An antibody may be polyclonal or monoclonal. A polyclonal antibody contains immunoglobulin molecules that differ in sequence of their complementarity determining regions (CDRs) and, therefore, typically recognize different epitopes of an antigen. Often a polyclonal antibody is derived from multiple different B cell lines each producing an antibody with a different specificity. A polyclonal antibody may be composed largely of several subpopulations of antibodies, each of which is derived from an individual B cell line. A monoclonal antibody is composed of individual immunoglobulin molecules that comprise CDRs with the same sequence, and, therefore, recognize the same epitope (i.e., the antibody is monospecific). Often a monoclonal antibody is derived from a single B cell line or hybridoma. An antibody may be a "humanized" antibody in which for example, a variable domain of rodent origin is fused to a constant domain of human origin or in which some or all of the complementarity-determining region amino acids often along with one or more framework amino acids are "grafted" from a rodent, e.g., murine, antibody to a human antibody, thus retaining the specificity of the rodent antibody.

"Body fluid" means any fluid in the body that may be assayed for the presence of complement proteins. Body fluids include, but are not limited to, whole blood, serum, plasma, urine, tears, saliva, wound exudate, broncheoalveolar lavage fluid, and cerebrospinal fluid (CSF).

"Control" refers to a sample having a known amount or level of a complement protein. In some embodiments, the control has a complement protein level comparable to that of an individual who does not have bacterial meningitis, such that a test sample having a complement protein level that is increased compared to the control is indicative of bacterial meningitis.

"Epitope" refers to the minimum portion of a molecule that is recognized by, and thus determines the immunospecificity of, an antibody that binds to such epitope. The term is also used herein to refer to the minimum portion of a molecule that is recognized by a non-antibody specific binding agent.

"Label" refers to a detectable moiety that facilitates the direct or indirect detection and/or quantitative or relative measurement of a molecule to which it is attached. A detectable label or detectable moiety often produces a signal such as fluorescence, chemiluminescence, radioactivity, color, magnetic or paramagnetic properties, etc., that renders it detectable, e.g., by the use of instruments that detect fluorescence, chemiluminescence, radioactivity, color, magnetic field, magnetic resonance, etc., or in some cases by visual inspection. The label may be, e.g., fluorescent substance; pigment; chemiluminescent or luminescent substance; colored substance; magnetic substance; or a non-magnetic metal particle such as gold colloid. In one embodiment, the detecting antibodies suitable for use in the instant methods and assays are conjugated to a colloidal gold label, which provides a color signal.

"Neoepitope" refers to an epitope that is generated or becomes detectable as a result of proteolytic cleavage of a complement component or cleavage product.

In certain embodiments of the assays and methods disclosed herein, the complement present in the body fluid sample tested is not substantially activated by the assay or method itself. "Not substantially activated," as used in this context, means that the methods and assays of the present invention are substantially free of in vitro activation caused by the test methods and/or materials. In this way, false positive test results are avoided, since the lateral flow immunoassay is rapid and requires less sample manipulation, thus avoiding many of the stimuli that contribute to in vitro complement activation.

"Point-of-care," as used herein, refers to a device or method that can be used or carried out at the bedside, in a doctor's office, in a healthcare or treatment facility or any place where a sample can be obtained from a subject to be tested. Point-of-care tests generally do not require shipping a sample to a laboratory for processing or the expertise of a skilled laboratory technician. The point-of-care methods and tests described herein allow a clinician to receive critical information at the patient's bedside, or at the site of evaluation or treatment, which can more efficiently and effectively direct patient care.

"Reader" refers to an instrument suitable for the detecting of the signal produced by the label. Various instruments are known in the art for the detection of label signals in diagnostic testing. In one embodiment of the present invention, the label is colloidal gold and the reader is an instrument suitable for the qualitative and/or quantitative detection of the color signal produced by the label. Suitable readers are available commercially from a variety of vendors, including BioAssay Works (Ijamsville, Md.), the ESE-Quant from Qiagen (Hilden, Germany), Easterline LRE (Nordlingen, Germany), and Detekt Biomedical (Austin, Tex.). In some specific embodiments, the reader is a hand-held reader that quantifies the amount or concentration of the complement protein(s) being evaluated.

As used herein, "serial" collection of samples refers to taking a separate sample (e.g., a CSF sample) from a subject over a course of time, e.g., minutes, hours, days, weeks, months, etc.)

As used herein, "effective amount" refers to an amount of a composition or formulation of this invention that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

The compositions of the present invention can also include other medicinal agents, pharmaceutical agents, carriers, diluents, immunostimulatory cytokines, etc. Actual methods of preparing such dosage forms are known, or will be apparent, to those skilled in this art. A dosage regimen can be one or more doses hourly, daily, weekly, monthly, yearly, etc. as deemed necessary to achieve the desired prophylactic and./or therapeutic effect to be achieved by administration of a composition of this invention to a subject. The efficacy of a particular dosage can be determined according to methods well known in the art.

Alternatively, pharmaceutical formulations of the present invention may be suitable for administration to the mucous membranes of a subject (e.g., via intranasal administration, buccal administration and/or inhalation). The formulations may be conveniently prepared in unit dosage form and may be prepared by any of the methods well known in the art.

Efficacy of the treatment methods of this invention can be determined according to well known protocols for determining the outcome of a treatment of a disease or infection of this invention. Determinants of efficacy of treatment, include, but are not limited to, overall survival, disease-free survival, improvement in symptoms, time to progression and/or quality of life, etc., as are well known in the art.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, delay of the onset of the disorder, disease or illness, and/or change in any of the clinical parameters of a disorder, disease or illness, etc., as would be well known in the art.

It is understood that the foregoing detailed description is given merely by way of illustration and that modifications and variations may be made therein without departing from the spirit and scope of the invention.

EXAMPLES

Example 1. C3 and Factor B (FB) as Bacterial Meningitis Biomarkers

Bacterial meningitis is characterized by high mortality and a high rate of persistent neurological impairment. Rapid etiologic diagnosis is essential for the adequate clinical management of patients with bacterial meningitis. Unfortunately, non-specific clinical symptoms and early laboratory findings often do not unequivocally differentiate between bacterial and aseptic meningitis. Therefore, the identification of a single discriminating parameter would be of high value in the differential diagnosis of acute meningitis.

This invention provides a method of diagnosing bacterial versus aseptic meningitis based on changes in the cerebrospinal fluid (CSF) levels of specific complement proteins, including, but not limited to C3, factor b (FB), MAC, C5b, C6, C7, C8, and C9 compared to normal CSF levels. The invention is based on the discovery that the CSF level of many complement proteins, which is normally low (nanogram to microgram range), increases one to two orders of magnitude or more in bacterial, but not aseptic or virally-induced meningitis. This increase allows ready discrimination between bacterial and aseptic meningitis using a variety of either quantitative or semi-quantitative assay platforms such as enzyme linked immunoassay (ELISA), multiplex or lateral flow assays, etc.

There is currently no inexpensive, point of care (POC) assay available to rapidly and accurately discriminate between bacterial and aseptic meningitis. The rapid assay system embodied in this invention could be used in clinical settings where CSF was drawn based on suspicion of bacterial meningitis. In such a platform, the assay would be used 1-2 million times per year in the United States, with comparable sized markets in Europe and Asia for diagnostic purposes.

Figure 2:
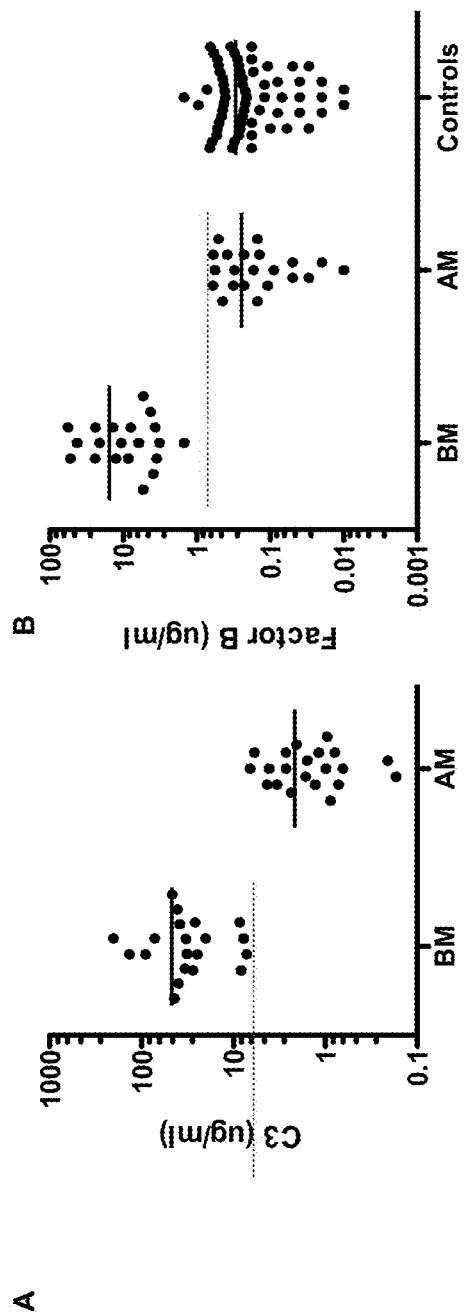
FIG. 2. Complement C3 and factor B (FB) concentrations in the CSF of patients with infectious meningitis or controls. C3 (Panel A) and FB (Panel B) CSF levels were measured by ELISA in 20 patients with confirmed bacterial meningitis, 21 patients with aseptic meningitis and 63 control patients. C3 and FB CSF levels in patients with bacterial meningitis were significantly elevated compared to those with aseptic meningitis or to controls ($p<0.001$, Wilcoxon rank sum test for all comparisons). The solid horizontal lines indicate the mean complement protein level for each group. The dotted line is the mean±2 SD of the aseptic meningitis group and is used for differentiation between bacterial versus aseptic meningitis.

ELISA for C3 and FB was performed on remnant CSF samples obtained from patients with confirmed bacterial or viral meningitis. It was found that both proteins were significantly elevated in bacterial meningitis compared to viral meningitis and controls (FIG. 2 and Table 2).

CSF levels in patients with bacterial meningitis were 21-fold higher than those in aseptic meningitis and almost 19-fold higher that controls. Factor B CSF levels in bacterial meningitis were even more elevated: 63-fold compared to aseptic meningitis and 53-fold compared to controls. Linear regression analysis comparing paired C3 and FB CSF levels in bacterial meningitis demonstrated a significant correlation between the two proteins ($r^2=0.33$, $p=0.008$), strongly suggesting common inflammatory mechanism(s) leading to their increase. In addition, both proteins discriminated between bacterial and viral meningitis with extremely high sensitivity and specificity (Table 2).

Currently discrimination between bacterial and aseptic meningitis is time-consuming and expensive. Gram staining, biochemistry and bacterial culture, currently the only tests for diagnosing bacterial meningitis, take hours to days for completion and have significant false positive rates. The current repertoire of laboratory tests used to diagnose bacterial meningitis costs at least $1000. In one embodiment of the present invention, a POC lateral flow assay would involve approximately 10-15 minutes and cost, e.g., around $100. This provides significant time and cost saving. Such a POC assay could, for example, be used in emergency rooms and free-standing clinics or healthcare facilities throughout the world.

Example 2. C9 as a Bacterial Meningitis Biomarker

A separate, but integral part of the pathogen clearance, the terminal complement pathway includes many different proteins. One of these, C9, is critical for the formation of the membrane attack complex (MAC), a large pore-forming complex capable of lysing host pathogens including many bacteria and enveloped viruses. The MAC is composed of five complement proteins, C5b, C6, C7, C8 and multiple C9 molecules (ranging from 12-18 per MAC). C9 molecules in the MAC form the actual pore structure that inserts into bacterial membranes resulting in their osmotic lysis.

C9 is distinct from C3 and FB as a biomarker for bacterial meningitis because its function is unrelated to and independent of both proteins.

C9 is an acute phase protein; i.e., its production is elevated in response to inflammation due to trauma or infection. C9 has been shown to be transported across the blood-brain barrier at low levels in the absence of infection. This process likely increases significantly during bacterial meningitis as a result of cytokine-mediated inflammation that weakens the blood-brain barrier. C9 production by several cells types in the central nervous system is increased in response to inflammation and infection.

Unlike C3 and factor B, many viral infections lead to a down-regulation of C9 production, which is a strategy used by some viruses to limit complement-mediated host defense functions. This enhances the relevance of C9 as a biomarker for bacterial meningitis since C9 levels are less likely to increase in viral infections, which should enhance the specificity and sensitivity of the assays of the present invention.

These unique features of C9 immunobiology, when paired with the ability of C3 and factor B to discriminate bacterial from aseptic meningitis provide for a diagnostic assay with additive and/or synergistic sensitivity.

Thus, in some embodiments of this invention, a CSF sample can be obtained from a subject (e.g., a subject in need thereof) and tested to determine an amount of C9 according to the methods and assays described herein.

Example 3. MAC as a Bacterial Meningitis Biomarker

A separate, but integral part of the pathogen clearance, the terminal complement pathway includes many different proteins. One of these, MAC is a large pore-forming complex capable of lysing host pathogens including many bacteria and enveloped viruses. The MAC is composed of five complement proteins, C5b, C6, C7, C8 and multiple C9 molecules (ranging from 12-18 per MAC). C9 molecules in the MAC form the actual pore structure that inserts into bacterial membranes resulting in their osmotic lysis.

MAC is distinct from C3 and FB as a biomarker for bacterial meningitis because its function is unrelated to and independent of both proteins.

Components of the MAC are acute phase proteins; i.e., their production is elevated in response to inflammation due to trauma or infection. Production of MAC subcomponents by several cells types in the central nervous system and other cell types is increased in response to inflammation and infection.

These unique features of MAC immunobiology alone allow it to discriminate bacterial from aseptic meningitis provide for a diagnostic assay. In addition, when paired with the ability of other complement components such as C3, to discriminate bacterial from aseptic meningitis provide for a diagnostic assay with additive and/or synergistic sensitivity.

Thus, in some embodiments of this invention, a CSF sample can be obtained from a subject (e.g., a subject in need thereof) and tested to determine an amount of MAC (e.g., C5, C6, C6, C8 and/or C9) according to the methods and assays described herein.

Example 4

In an exemplary embodiment, the present invention provides a method of diagnosing bacterial infection in subjects with indwelling shunts or extra-ventricular devices (EVDs) based on changes in the cerebrospinal fluid (CSF) levels of specific complement proteins, including, but not limited to, C3, C5b-9 (MAC) and factor B as compared to control CSF levels. This embodiment is based on the observation that the CSF level of many complement proteins which are normally low (nanogram to low microgram range), can increase several orders of magnitude in CSF of confirmed bacterial infection. This dramatic increase allows for a rapid determination of shunt/EVD infection/meningitis using a variety of either quantitative or semi-quantitative assay platforms such as ELISA, multiplex or lateral flow assays. There is currently no inexpensive, point-of-care (POC) assay available to rapidly and accurately diagnose a shunt/EVD infection.

Upon application of the invention to a rapid assay system, the assay could be used in any clinical setting where CSF was drawn based on suspicion of shunt/EVD infection. In such a platform, the assay would be used ~1 million times per year in the U.S., with comparable-sized markets in Europe and Asia for diagnostic purposes.

Figure 3:
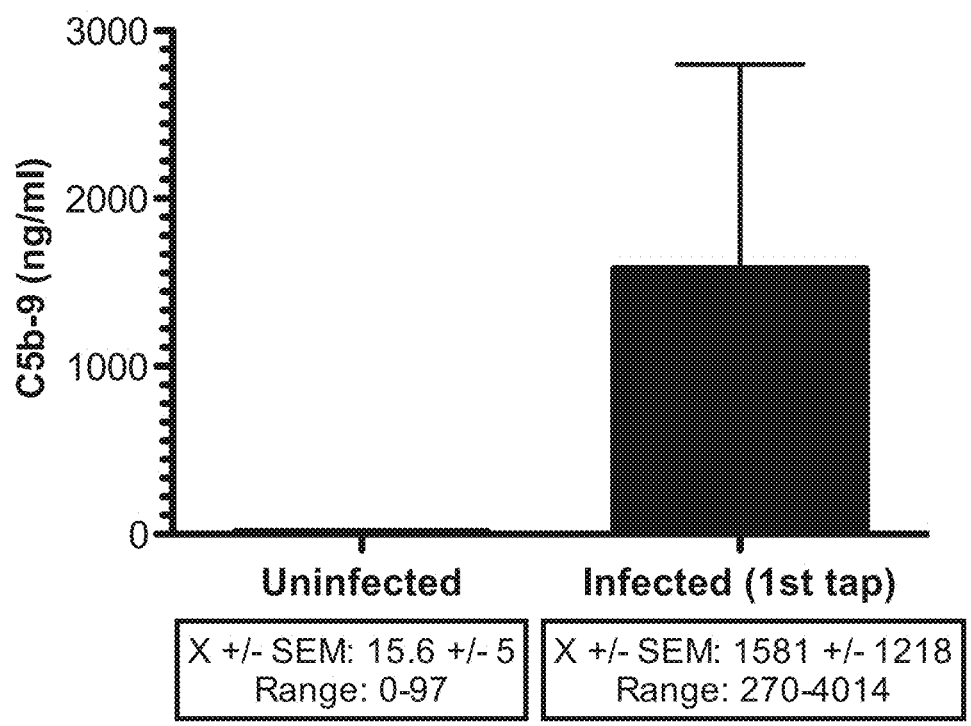
FIG. 3. C5b-9 (MAC) concentrations in the CSF of shunt/EVD patients with and without infection. MAC CSF levels were measured by ELISA in 3 patients with confirmed bacterial infection and 24 patients without infection. MAC CSF levels in patients with bacterial infection were significantly elevated compared to those without infection ($p<0.0002$, unpaired t-test). The line is the mean±2 SD of the infected group and is used for differentiation between the infected and uninfected groups.
Figure 5:
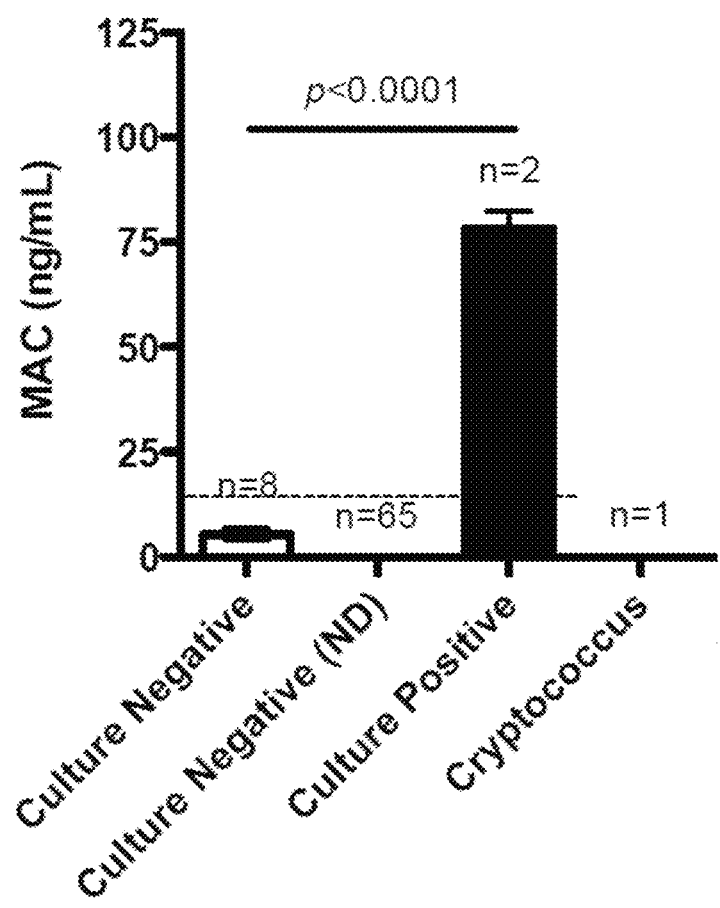
FIG. 5. Changes in soluble CSF MAC levels in patients with confirmed bacterial, aseptic or cryptococcal infection. MAC CSF levels were measured by ELISA in 2 patients with confirmed bacterial meningitis (as assessed by bacterial culture), 73 aseptic patients (negative by bacterial culture) and 1 patient with confirmed cryptococcal infection. MAC CSF levels in patients with bacterial infection were significantly elevated compared to aseptic patients with detectable MAC levels ($p<0.0001$, unpaired t-test). The dotted line represents the mean±2 SD of detectable MAC CSF levels in aseptic patients and is used for discrimination between bacterial and aseptic meningitis. Samples were diluted as needed to obtain quantifiable data and duplicate samples were assayed according to the manufacturer's instructions.

We performed ELISAs for MAC on CSF samples obtained from pediatric neurosurgery subjects with shunts or EVDs on suspicion of bacterial infection. We found that MAC levels were markedly upregulated in subjects with confirmed bacterial infection compared to those with no infection (control subjects) (FIGS. 3 and 5, Table 3). The mean MAC CSF levels on the first draw of CSF in patients with shunt/EVD infections (n=3) were 100-fold higher than those without infection (n=24). These data indicated that the MAC and potentially other complement proteins or activation fragments have significant potential as diagnostic markers for shunt/EVD infection.

Currently, diagnosis of shunt/EVD infections is time-consuming and expensive. Gram staining, biochemistry, and bacterial culture, currently the only tests for diagnosing bacterial meningitis, take hours to days for completion and have significant false-positive rates. The current repertoire of laboratory tests used to determine if the CSF is infected costs at least $1,000. In some embodiments of the present invention, employing a POC lateral flow assay would be rapid (e.g., test results could be available in approximately 10-15 minutes and low cost (e.g., around $100). This provides a significant time and cost savings for the patient. In addition, a POC biomarker assay would allow for better patient management.

The invention once applied to a POC rapid assay method would have significant market potential. It could be used in operating rooms and clinics throughout the world.

Example 5

Figure 4:
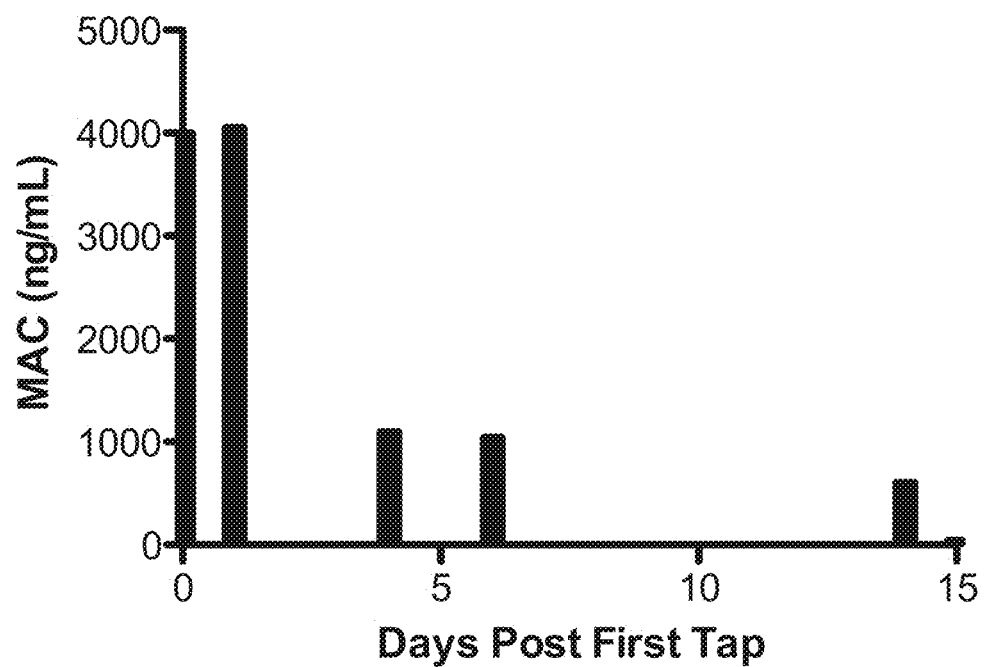
FIG. 4. Changes in CSF MAC levels as a function of time in a patient with a shunt infection. CSF MAC levels were quantitated using an ELISA specific for soluble MAC (Quidel Corp., San Diego, Calif.). Samples were diluted as needed to obtain quantifiable data and duplicate samples assayed according to the manufacturer's instructions.

To determine the value of repeated monitoring of CSF from patients with confirmed shunt infection, we assayed for the CSF levels of MAC at various times points after the initial tap for up to fifteen days. The MAC CSF level on the initial tap was greater than 400 times the normal level observed in non-infected patients (FIG. 4). Intravenous antibiotic therapy was instituted and the patient was repeatedly tapped to follow the effectiveness of the antibiotic treatment. The CSF levels of MAC levels declined over time as the patient improved and the infection cleared. These data indicate that following the CSF level of MAC, and possibly other complement activation components, may be clinically useful in monitoring effectiveness of antibiotic and other treatment modalities in shunt infections.

Example 6. MAC and C3 as Indicators of Shunt Failure

In an exemplary embodiment, the present invention provides a method of discriminating shunt failure (symptomatic ventricular enlargement, SVE) from bacterial infection and/or asymptomatic ventricular enlargement (AVE) in subjects with indwelling shunts or extra-ventricular devices (EVDs) based on changes in the cerebrospinal fluid (CSF) levels of specific complement proteins, including, but not limited to, C3, C5b-9 (MAC) and factor B as compared to control CSF levels. This embodiment is based on the observation that the CSF level of many complement proteins which are normally low (nanogram range), can increase 8-10-fold in patients with SVE compared to those with AVE, but be several orders of magnitude lower than in CSF of confirmed bacterial infection. This distinct range of complement levels allows for a rapid determination of shunt/EVD failures versus infection/meningitis using a variety of either quantitative or semi-quantitative assay platforms such as ELISA, multiplex or lateral flow assays. There is currently no inexpensive, point-of-care (POC) assay available to rapidly and accurately diagnose a shunt failure.

Upon application of the invention to a rapid assay system, the assay could be used in any clinical setting where CSF was drawn based on suspicion of shunt failure. In such a platform, the assay would be used ~1 million times per year in the U.S., with comparable-sized markets in Europe and Asia for diagnostic purposes.

Figure 6:
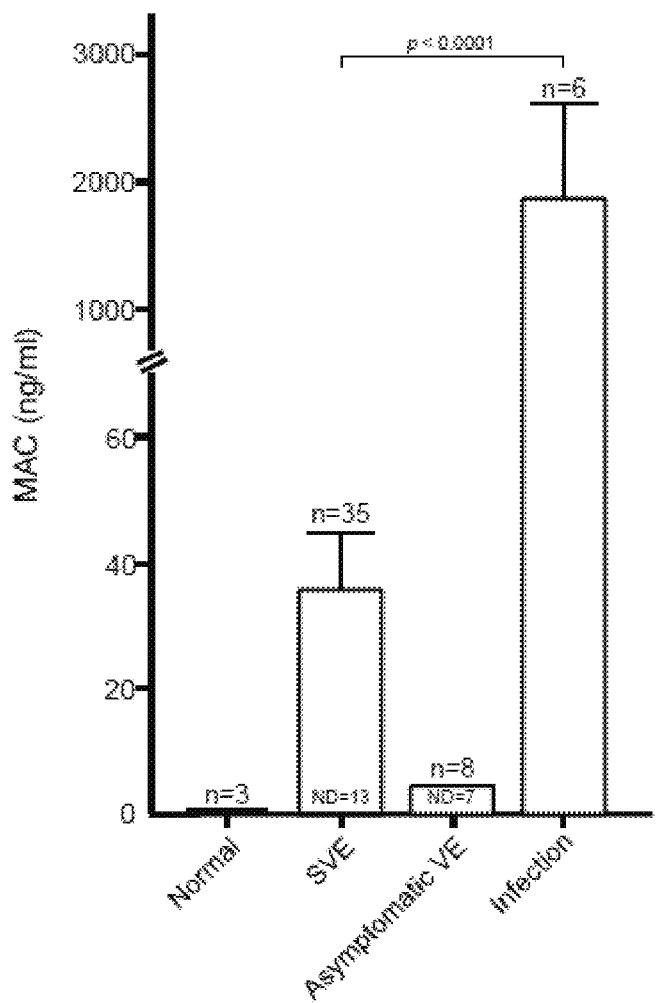
FIG. 6. Changes in CSF MAC levels in patients with shunt infections, asymptomatic ventricular enlargement (VE), symptomatic ventricular enlargement (SVE, "shunt failure") and normals. CSF MAC levels in normal patients were undetectable by ELISA in 3 patients. Similarly, CSF MAC levels were essentially undetectable in asymptomatic VE patients (only 1 in 8 patients had detectable MAC levels). In contrast, SVE patients had elevated CSF MAC levels with MAC detectable in 22 of 35 patients, while CSF MAC levels in 6 patients with confirmed bacterial infection were significantly elevated compared to SVE patients ($p<0.0001$, unpaired t-test). Samples were diluted as needed to obtain quantifiable data and duplicate samples were assayed according to the manufacturer's instructions.
Figure 7:
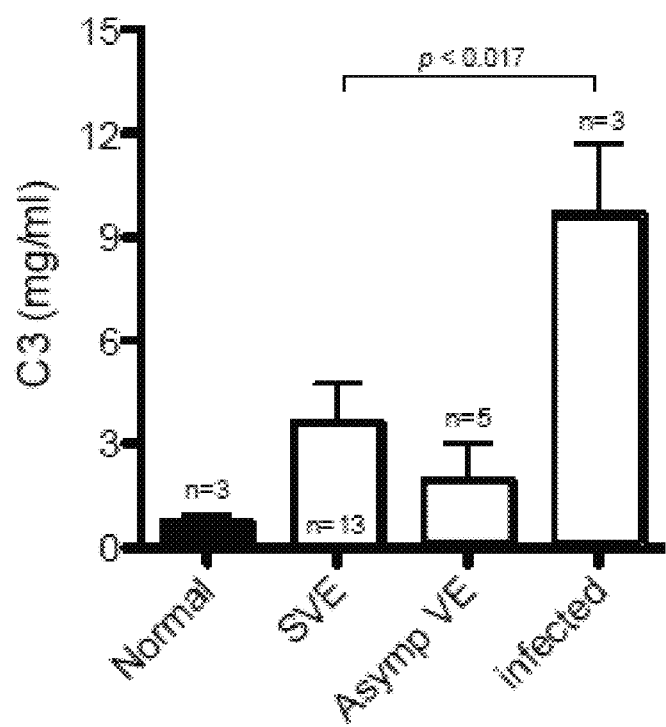
FIG. 7. Changes in CSF C3 levels in patients with shunt infections, asymptomatic ventricular enlargement (VE), symptomatic ventricular enlargement (SVE, "shunt failure") and normals. CSF C3 levels in normal and asymptomatic VE patients were low as assessed by ELISA. In contrast, SVE patients had elevated CSF C3 levels with C3 detectable in all patients, while CSF C3 levels in 3 patients with confirmed bacterial infection were significantly elevated compared to SVE patients ($p<0.017$, unpaired t-test). Samples were diluted as needed to obtain quantifiable data and duplicate samples were assayed according to the manufacturer's instructions.

We performed ELISAs for MAC on CSF samples obtained from pediatric neurosurgery subjects with shunts or EVDs on suspicion of shunt failure or bacterial infection. We found that MAC levels were markedly lower in subjects with confirmed shunt failure compared to those with bacterial infection (FIG. 6). The mean MAC CSF levels in CSF in patients with shunt failure (n=35) was 8-10-fold higher than those with AVE but 30-40-fold lower than patients with bacterial infection (n=6). These data indicated that the MAC has significant potential as diagnostic markers for shunt failures. Similarly we performed ELISAs for C3 on CSF samples obtained from pediatric neurosurgery subjects with shunts or EVDs on suspicion of shunt failure or bacterial infection. We found that C3 levels were significantly lower in subjects with confirmed shunt failure compared to those with bacterial infection (FIG. 7). The mean C3 CSF levels in CSF in patients with shunt failure (n=13) was 2-fold higher than those with AVE but 3-fold lower than patients with bacterial infection (n=3). These data indicated that the C3 has significant potential as diagnostic markers for shunt failures.

Currently, diagnosis of shunt failure is time-consuming and expensive. Gram staining, biochemistry, and bacterial culture, to determine if the patient has a low grade infection as opposed to shunt failure, takes hours to days for completion and have significant false-positive rates. The current repertoire of laboratory tests used to determine if the CSF is infected costs at least $1,000. Patients with suspected shunt failure also undergo expensive imaging studies to determine if there is ventricular enlargement characteristic or shunt failure. In some embodiments of the present invention, employing a POC lateral flow assay would be rapid (e.g., test results could be available in approximately 10-15 minutes and low cost (e.g., around $100). This provides a significant time and cost savings for the patient. In addition, a POC biomarker assay would allow for better patient management.

The invention once applied to a POC rapid assay method would have significant market potential. It could be used in operating rooms and clinics throughout the world.

All references cited herein, including non-patent publications, patent applications, GenBank® Database accession numbers and patents, are incorporated by reference herein in their entireties to the same extent as if each was individually and specifically indicated to be incorporated by reference, and was reproduced in its entirety herein.

While particular embodiments of the present invention have been illustrated and described, it would be understood by one skilled in the art that various other changes and modifications can be made without departing from the spirit and scope of the invention. It is, therefore, intended to cover in the appended claims all such changes and modifications that are within the scope of this invention.

TABLE 1

Antibodies to C3

| Species | Antigen | Supplier |
|---|---|---|
| mouse | C3a | Hycult (HM2075) |
| mouse | C3a | Quidel (A203) |
| chicken | C3a | GenTex (GTX78198) |
| mouse | C3a | Quidel (A203) |
| goat | C3a | SantaCruz (sc17237) |
| mouse | C3a | Hycult (HM2073) |
| mouse | C3a | Hycult (HM2074) |
| chicken | C3a | Abcam (ab48580) |
| mouse | C3a | Hycult (HM2073) |
| mouse | C3a | Quidel (A203) |
| chicken | C3a | Abcam (ab48580) |
| mouse | C3a | Hycult (HM2073) |
| goat | C3a | SantaCruz (sc17237) |
| rabbit | C3d | Abcam (ab15981) |
| rabbit | C3d | Abcam (ab15981) |
| rabbit | C3d | Abcam (ab15981) |
| rabbit | C3d | Abcam (ab15981) |
| rabbit | C3d | Abcam (ab15981) |
| rabbit | C3d | Abcam (ab15981) |
| goat | C3 | MP Biomedicals (55237) |
| goat | C3 | MP Biomedicals (55237) |
| rabbit | C3d | Abcam (ab15981) |
| rabbit | C3d | Abcam (ab15981) |
| rabbit | C3d | Abcam (ab15981) |
| rabbit | C3d | Abcam (ab15981) |
| rabbit | C3d | Abcam (ab15981) |
| rabbit | C3d | Abcam (ab15981) |
| chicken | C3a | Abcam (ab48580) |
| chicken | C3a | Abcam (ab48580) |
| goat | C3 | MP Biomedicals (55237) |
| goat | C3 | MP Biomedicals (55237) |
| goat | C3 | MP Biomedicals (55237) |
| mouse | C3a | Quidel (A2103) |
| chicken | C3a | GenTex (GTX78198) |
| goat | C3a | SantaCruz (sc17237) |
| chicken | C3a | Abcam (ab48580) |
| mouse | C3a | Hycult (HM2073) |
| mouse | C3a | Hycult (HM2074) |
| mouse | iC3b | Quidel (A209) |
| mouse | iC3b | AbD serotec (MCA2607) |
| mouse | iC3b | AbD serotec (MCA2607) |
| mouse | iC3b | Quidel (A209) |
| mouse | iC3b | Quidel (A209) |
| mouse | iC3b | Quidel (A209) |
| mouse | iC3b | Quidel (A209) |
| rat | iC3b | Hycult (HM2199) |
| rat | iC3b | Hycult (HM2199) |
| rat | iC3b | Hycult (HM2199) |
| rat | iC3b | Hycult (HM2199) |
| rat | iC3b | Hycult (HM2199) |
| mouse | active C3 | Hycult (HM2168) |
| mouse | active C3 | Hycult (HM2168) |
| mouse | active C3 | Hycult (HM2257) |
| mouse | active C3 | Hycult (HM2257) |
| mouse | C3 alpha | Meridian (H54189M) |
| mouse | neo C3d | Quidel (A250) |
| goat | C3 | MP Biomedicals (55237) |
| goat | C3 | MP Biomedicals (55237) |
| rabbit | C3d | Abcam (ab15981) |
| rabbit | C3d | Abcam (ab15981) |
| rat | C3d | Hycult (HM2198) |
| rat | C3g | Hycult (HM2199) |
| mouse | neo C3d | Quidel (A250) |
| goat | C3 | MP Biomedicals (55237) |
| mouse | active C3 | Hycult (HM2168) |
| mouse | Active C3 | Hycult (HM2257) |
| mouse | iC3b | Quidel (A209) |
| mouse | Neo C3d | Quidel (A250) |
| goat | C3 | MP Biomedicals (55237) |
| rat | C3g | Hycult (HM 2199) |
| goat | C3 | MP Biomedicals (55237) |
| rat | C3g | Hycult (HM 2199) |
| goat | C3 | MP Biomedicals (55237) |
| rat | C3g | Hycult (HM 2199) |

TABLE 2

Statistical parameters for C3 and factor B in bacterial versus aseptic meningitis

|  | C3 | | | Factor B | | |
| --- | --- | --- | --- | --- | --- | --- |
|  | BM | AM | Controls | BM | AM | Controls |
| Mean ± SE (µg/ml) | 47 ± 10.8 | 2.2 ± 0.4 | 2.5 ± 0.3 | 15.7 ± 3.8 | 0.25 ± 0.04 | 0.3 ± 0.03 |
| Sensitivity |  | 100% |  |  | 100% |  |
| Sencificity |  | 95% |  |  | 100% |  |

BM, bacterial meningitis,
AM, aseptic meningitis

TABLE 3

Statistical parameters for MAC in shunt/EVD infections

|  | Shunt infection | Controls |
| --- | --- | --- |
| n | 3 | 24 |
| Mean ± SEM (ng/ml) | 1581 ± 1218 | 15.6 ± 5 |
| Range | 270-4014 | 0-97 |

What is claimed is:

1. A method of guiding a treatment for an infection associated with an indwelling shunt and/or extra-ventricular device in a subject in need thereof, comprising:
   a) measuring the amount of complement membrane attack complex (MAC) and optionally complement C3, complement factor B, complement C5b, complement C6, complement C7, complement C8, and/or complement C9 in a cerebrospinal fluid (CSF) sample obtained from the subject prior to administration of an appropriate treatment for the infection associated with an indwelling shunt and/or extra-ventricular device;
   b) administering the appropriate treatment for an infection associated with an indwelling shunt and/or extra-ventricular device to the subject;
   c) measuring the amount of complement MAC and optionally complement C3, complement factor B, complement C5b, complement C6, complement C7, complement C8, and/or complement C9 in a cerebrospinal fluid (CSF) sample obtained from the subject at one or more time points after (b);
   d) guiding the treatment of the subject for the infection associated with an indwelling shunt and/or extra-ventricular device using the measurement(s) of (c) such that an increase or no change in the amount(s) measured in (c) relative to the amount(s) measured in (a) leads to a subsequent enhancement of the treatment, and a decrease in the amount(s) measured in (c) relative to the amount(s) measured in (a) leads to no change or a subsequent reduction of the treatment.

2. The method of claim 1, wherein the amount of complement MAC, the amount of complement C9 and the amount of complement C3 in the CSF sample are measured.

3. The method of claim 1, wherein the amount of complement MAC, the amount of complement C9 and the amount of complement factor B in the CSF are measured.

4. The method of claim 1, wherein the amount of complement MAC, the amount of complement C9 and the amount of complement C5b in the CSF sample are measured.

5. The method of claim 1, wherein the amount of complement MAC, the amount of complement C9 and the amount of complement C6 in the CSF sample are measured.

6. The method of claim 1, wherein the amount of complement MAC, the amount of complement C9 and the amount of complement C7 in the CSF sample are measured.

7. The method of claim 1, wherein the amount of complement MAC, the amount of complement C9 and the amount of complement C8 in the CSF sample are measured.

8. The method of claim 1, wherein the amount of complement MAC, the amount of complement C8 and the amount of complement C3 in the CSF sample are measured.

9. The method of claim 1, wherein the amount of complement MAC, the amount of complement C8 and the amount of complement factor B in the CSF are measured.

10. The method of claim 1, wherein the amount of complement MAC, the amount of complement C8 and the amount of complement C5b in the CSF sample are measured.

11. The method of claim 1, wherein the amount of complement MAC, the amount of complement C8 and the amount of complement C6 in the CSF sample are measured.

12. The method of claim 1, wherein the amount of complement MAC, the amount of complement C8 and the amount of complement C7 in the CSF sample are measured.

13. The method of claim 1, wherein the amount of complement MAC, the amount of complement C7 and the amount of complement C3 in the CSF sample are measured.

14. The method of claim 1, wherein the amount of complement MAC, the amount of complement C7 and the amount of complement factor B in the CSF are measured.

15. The method of claim 1, wherein the amount of complement MAC, the amount of complement C7 and the amount of complement C5b in the CSF sample are measured.

16. The method of claim 1, wherein the amount of complement MAC, the amount of complement C7 and the amount of complement C6 in the CSF sample are measured.

17. The method of claim 1, wherein the amount of complement MAC, the amount of complement C6 and the amount of complement C3 in the CSF sample are measured.

18. The method of claim 1, wherein the amount of complement MAC, the amount of complement C6 and the amount of complement factor B in the CSF are measured.

19. The method of claim 1, wherein the amount of complement MAC, the amount of complement C6 and the amount of complement C5b in the CSF sample are measured.

20. The method of claim 1, wherein the amount of complement MAC, the amount of complement C5b and the amount of complement C3 in the CSF sample are measured.

21. The method of claim 1, wherein the amount of complement MAC, the amount of complement C5b and the amount of complement factor B in the CSF are measured.

22. The method of claim 1, wherein the amount of complement MAC and the amount of complement factor B and the amount of complement C3 in the CSF are measured.

23. The method of claim 1, wherein the amount of complement MAC, the amount of complement C9 and the amount of complement factor B and the amount of complement C3 in the CSF are measured.

24. The method of claim 1, wherein the measuring is carried out with a point of care (POC) rapid assay system.

25. The method of claim 1, wherein the measuring is carried out with a lateral flow system.

26. The method of claim 1, wherein the measuring is carried out with an immunoassay.

27. The method of claim 1, wherein the measuring is carried out with an enzyme-linked immunosorbent assay (ELISA).

28. The method of claim 1, wherein the appropriate treatment for an infection associated with an indwelling shunt and/or extra-ventricular device comprises one or more of removal of the indwelling shunt or extra-ventricular device, flushing of the indwelling shunt and/or extra-ventricular device, administration of antibiotics, steroids, and/or anti-inflammatory agents, and replacement of the indwelling shunt and/or extra-ventricular device.

29. A method of treating a subject with an infection associated with an indwelling shunt and/or extra-ventricular device based on the identification of infection associated with an indwelling shunt and/or extra-ventricular device, comprising:
   a) measuring the amount of complement MAC and optionally complement C3, complement factor B, complement C5b, complement C6, complement C7, complement C8, and/or complement C9 in a cerebrospinal fluid (CSF) sample obtained from the subject, wherein an amount of complement MAC and optionally complement C3, complement factor B, complement C5b, complement C6, complement C7, complement C8, and/or complement C9 measured in (a) that is greater than a threshold amount of complement MAC and optionally complement C3, complement factor B, complement C5b, complement C6, complement C7, complement C8, and/or complement C9 identifies an infection in the subject associated with the indwelling shunt and/or extra-ventricular device; and
   b) treating the subject identified in (a) for the infection associated with the indwelling shunt and/or extra-ventricular device with an appropriate treatment for infection associated with an indwelling shunt and/or extra-ventricular based on the identification of an infection associated with an indwelling shunt and/or extra-ventricular device.

30. The method of claim 29, wherein complement proteins measured in the CSF sample are:
   complement MAC, complement C9 and complement C3;
   complement MAC, complement C9 and complement factor B;
   complement MAC, complement C9 and complement C5b;
   complement MAC, complement C9 and complement C6;
   complement MAC, complement C9 and complement C7;
   complement MAC, complement C9 and complement C8;
   complement MAC, complement C8 and complement C3;
   complement MAC, complement C8 and complement factor B;
   complement MAC, complement C8 and complement C5b;
   complement MAC, complement C8 and complement C6;
   complement MAC, complement C8 and complement C7;
   complement MAC, complement C7 and complement C3;
   complement MAC, complement C7 and complement factor B;
   complement MAC, complement C7 and complement C5b;
   complement MAC, complement C7 and complement C6;
   complement MAC, complement C6 and complement C3;
   complement MAC, complement C6 and complement factor B;
   complement MAC, complement C6 and complement C5b;
   complement MAC, complement C5b and complement C3;
   complement MAC, complement C5b and complement factor B;
   complement MAC, complement factor B and complement C3; or
   complement MAC, complement C9 and complement factor B.

31. The method of claim 29, wherein the appropriate treatment for an infection associated with an indwelling shunt and/or extra-ventricular device comprises one or more of removal of the indwelling shunt or extra-ventricular device, flushing of the indwelling shunt and/or extra-ventricular device, administration of antibiotics, steroids, and/or anti-inflammatory agents, and replacement of the indwelling shunt and/or extra-ventricular device.

32. A method of treating a subject with an infection associated with an indwelling shunt and/or extra-ventricular device, comprising treating the subject identified as having an amount of complement MAC and optionally complement C3, complement factor B, complement C5b, complement C6, complement C7, complement C8, and/or complement C9 measured in a cerebrospinal fluid (CSF) sample that is greater than a threshold amount of complement MAC and optionally complement C3, complement factor B, complement C5b, complement C6, complement C7, complement C8, and/or complement C9.

33. The method of claim 32, wherein complement proteins measured in the CSF sample are:
complement MAC, complement C9 and complement C3;
complement MAC, complement C9 and complement factor B;
complement MAC, complement C9 and complement C5b;
complement MAC, complement C9 and complement C6;
complement MAC, complement C9 and complement C7;
complement MAC, complement C9 and complement C8;
complement MAC, complement C8 and complement C3;
complement MAC, complement C8 and complement factor B;
complement MAC, complement C8 and complement C5b;
complement MAC, complement C8 and complement C6;
complement MAC, complement C8 and complement C7;
complement MAC, complement C7 and complement C3;
complement MAC, complement C7 and complement factor B;
complement MAC, complement C7 and complement C5b;
complement MAC, complement C7 and complement C6;
complement MAC, complement C6 and complement C3;
complement MAC, complement C6 and complement factor B;
complement MAC, complement C6 and complement C5b;
complement MAC, complement C5b and complement C3;
complement MAC, complement C5b and complement factor B;
complement MAC, complement factor B and complement C3; or
complement MAC, complement C9 and complement factor B.

* * * * *

UNITED STATES PATENT AND TRADEMARK OFFICE
CERTIFICATE OF CORRECTION

PATENT NO. : 10,830,774 B2
APPLICATION NO. : 15/469986
DATED : November 10, 2020
INVENTOR(S) : Barnum et al.

Page 1 of 1

It is certified that error appears in the above-identified patent and that said Letters Patent is hereby corrected as shown below:

In the Specification

Column 1, Line 8: Please correct "U.s. application" to read -- U.S. Application --

Column 21, Line 64: Please correct "Abeam" to read -- Abcam --

Column 21, Line 66: Please correct "Abeam" to read -- Abcam --

Column 21, Line 67: Please correct "Abeam" to read -- Abcam --

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial
<220> FEATURE:
<223> OTHER INFORMATION: C9 Epitope

<400> SEQUENCE: 1

Cys Met Pro Ile Pro Val Ser Arg Glu Glu Gln Glu Gln His Tyr Pro
1               5                   10                  15

Ile Pro Ile Asp
            20
```